(12) United States Patent
Patterson et al.

(10) Patent No.: US 9,498,349 B2
(45) Date of Patent: Nov. 22, 2016

(54) EXPANDABLE SPINAL IMPLANT WITH EXPANSION WEDGE AND ANCHOR

(71) Applicant: Titan Spine, LLC, Mequon, WI (US)

(72) Inventors: Chad J. Patterson, Port Washington, WI (US); Peter F. Ullrich, Jr., Neenah, WI (US)

(73) Assignee: Titan Spine, LLC, Mequon, WI (US)

( * ) Notice: Subject to any disclaimer, the term of this patent is extended or adjusted under 35 U.S.C. 154(b) by 363 days.

(21) Appl. No.: 14/043,171

(22) Filed: Oct. 1, 2013

(65) Prior Publication Data

US 2014/0100662 A1 Apr. 10, 2014

Related U.S. Application Data

(60) Provisional application No. 61/711,403, filed on Oct. 9, 2012.

(51) Int. Cl.
*A61F 2/44* (2006.01)
*A61F 2/46* (2006.01)
*A61F 2/30* (2006.01)

(52) U.S. Cl.
CPC .............. *A61F 2/447* (2013.01); *A61F 2/4455* (2013.01); *A61F 2/4465* (2013.01); *A61F 2/4611* (2013.01); *A61F 2002/3084* (2013.01); *A61F 2002/30266* (2013.01); *A61F 2002/30281* (2013.01); *A61F 2002/30383* (2013.01); *A61F 2002/30401* (2013.01); *A61F 2002/30481* (2013.01); *A61F 2002/30492* (2013.01); *A61F 2002/30556* (2013.01); *A61F 2002/30579* (2013.01); *A61F 2002/30779* (2013.01); *A61F 2002/30787* (2013.01); *A61F 2002/30838* (2013.01);

(Continued)

(58) Field of Classification Search
CPC ........ A61F 2/44; A61F 2/4455; A61F 2/446; A61F 2/4465; A61F 2/447; A61F 2002/30878; A61F 2002/30884
See application file for complete search history.

(56) References Cited

U.S. PATENT DOCUMENTS 4,314,876 A 2/1982 Kremer et al.
4,834,757 A 5/1989 Brantigan
(Continued)

FOREIGN PATENT DOCUMENTS

EP 0599419 6/1994
EP 0916323 5/1999
(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Mary Hoffman
(74) *Attorney, Agent, or Firm* — Stradley Ronon Stevens & Young, LLP

(57) ABSTRACT

An interbody spinal implant system includes an implant having separate, but joined top and bottom portions, a socket for receiving an expansion wedge, an expansion wedge, and an anchor pin. The anchor pin includes at least two prongs having a plurality of ridges or teeth. The top portion and the bottom portion each include a slot for receiving a prong of the anchor pin. A movable joint joins the top and bottom portions and allows the top and bottom portions to move vertically relative to each other.

17 Claims, 18 Drawing Sheets

(52) U.S. Cl.
CPC ............... *A61F2002/30906* (2013.01); *A61F 2002/30925* (2013.01); *A61F 2002/4475* (2013.01); *A61F 2310/00023* (2013.01)

(56) References Cited

U.S. PATENT DOCUMENTS

| | | | |
|---|---|---|---|
| 4,904,261 A | 2/1990 | Dove et al. | |
| 5,015,247 A | 5/1991 | Michelson | |
| 5,071,437 A | 12/1991 | Steffee | |
| 5,258,098 A | 11/1993 | Wagner et al. | |
| 5,306,308 A | 4/1994 | Gross et al. | |
| 5,306,309 A | 4/1994 | Wagner et al. | |
| 5,425,772 A | 6/1995 | Brantigan | |
| 5,443,514 A | 8/1995 | Steffee | |
| 5,456,723 A | 10/1995 | Steinemann et al. | |
| 5,507,815 A | 4/1996 | Wagner et al. | |
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,755,798 A | 5/1998 | Papavero et al. | |
| 5,766,252 A | 6/1998 | Henry et al. | |
| 5,776,199 A | 7/1998 | Michelson | |
| 5,849,004 A * | 12/1998 | Bramlet | A61B 17/0401 606/232 |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlapfer et al. | |
| 6,080,158 A | 6/2000 | Lin | |
| 6,086,613 A | 7/2000 | Camino et al. | |
| 6,096,107 A | 8/2000 | Caracostas et al. | |
| 6,102,950 A * | 8/2000 | Vaccaro | A61F 2/447 606/247 |
| 6,113,638 A * | 9/2000 | Williams | A61F 2/442 128/898 |
| 6,123,705 A | 9/2000 | Michelson | |
| 6,143,032 A | 11/2000 | Schafer et al. | |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,425,920 B1 | 7/2002 | Hamada | |
| 6,432,140 B1 | 8/2002 | Lin | |
| 6,436,102 B1 | 8/2002 | Ralph et al. | |
| 6,447,544 B1 | 9/2002 | Michelson | |
| 6,447,546 B1 * | 9/2002 | Bramlet | A61F 2/446 623/17.11 |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,412 B2 | 3/2006 | Ferreira et al. | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Liu et al. | |
| 7,128,760 B2 | 10/2006 | Michelson | |
| 7,137,997 B2 | 11/2006 | Paul | |
| 7,141,068 B2 | 11/2006 | Ross et al. | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,238,203 B2 | 7/2007 | Bagga et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,062,304 B2 | 11/2011 | Blain et al. | |
| 8,062,374 B2 * | 11/2011 | Markworth | A61F 2/447 623/17.11 |
| 8,100,955 B2 | 1/2012 | Blain et al. | |
| 8,142,355 B2 | 3/2012 | Blain et al. | |
| 8,172,854 B2 | 5/2012 | Blain et al. | |
| 8,262,737 B2 | 9/2012 | Bagga et al. | |

(56) References Cited

U.S. PATENT DOCUMENTS

| | | | |
|---|---|---|---|
| 8,523,946 B1* | 9/2013 | Swann | A61F 2/447 623/17.11 |
| 8,628,578 B2* | 1/2014 | Miller | A61F 2/4425 623/17.11 |
| 8,894,652 B2* | 11/2014 | Seifert | A61B 17/1617 606/79 |
| 2001/0014826 A1 | 8/2001 | Biedermann et al. | |
| 2001/0016777 A1 | 8/2001 | Biscup | |
| 2001/0039454 A1 | 11/2001 | Ricci et al. | |
| 2001/0047208 A1 | 11/2001 | Michelson | |
| 2002/0049497 A1 | 4/2002 | Mason | |
| 2002/0087212 A1 | 7/2002 | James et al. | |
| 2002/0099443 A1 | 7/2002 | Messerli et al. | |
| 2002/0128716 A1 | 9/2002 | Cohen et al. | |
| 2002/0138142 A1 | 9/2002 | Castro et al. | |
| 2002/0156529 A1 | 10/2002 | Li et al. | |
| 2002/0161443 A1 | 10/2002 | Michelson | |
| 2002/0173854 A1 | 11/2002 | Amrich | |
| 2002/0188294 A1 | 12/2002 | Couture et al. | |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0153975 A1 | 8/2003 | Byrd, III et al. | |
| 2003/0176925 A1 | 9/2003 | Paponneau | |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 | 10/2003 | Berry et al. | |
| 2004/0073314 A1 | 4/2004 | White et al. | |
| 2004/0117019 A1 | 6/2004 | Trieu et al. | |
| 2004/0117020 A1 | 6/2004 | Frey et al. | |
| 2004/0122518 A1 | 6/2004 | Rhoda | |
| 2004/0127993 A1 | 7/2004 | Kast et al. | |
| 2004/0134886 A1 | 7/2004 | Wagner et al. | |
| 2004/0153154 A1 | 8/2004 | Dinkelacker | |
| 2004/0153160 A1 | 8/2004 | Carrasco | |
| 2004/0162616 A1 | 8/2004 | Simonton et al. | |
| 2004/0167632 A1 | 8/2004 | Wen et al. | |
| 2004/0186570 A1* | 9/2004 | Rapp | A61F 2/4455 623/17.11 |
| 2004/0210309 A1 | 10/2004 | Denzer et al. | |
| 2004/0230306 A1 | 11/2004 | Hoeck et al. | |
| 2004/0254644 A1* | 12/2004 | Taylor | A61F 2/4425 623/17.13 |
| 2004/0265780 A1 | 12/2004 | Robb et al. | |
| 2004/0267367 A1 | 12/2004 | O'Neil | |
| 2005/0021150 A1 | 1/2005 | Michelson | |
| 2005/0027360 A1 | 2/2005 | Webb et al. | |
| 2005/0038512 A1 | 2/2005 | Michelson | |
| 2005/0060034 A1 | 3/2005 | Berry et al. | |
| 2005/0075734 A1 | 4/2005 | Fulton et al. | |
| 2005/0085913 A1 | 4/2005 | Fraser et al. | |
| 2005/0119758 A1 | 6/2005 | Alexander et al. | |
| 2005/0131416 A1 | 6/2005 | Jansen et al. | |
| 2005/0147942 A1 | 7/2005 | Hall | |
| 2005/0159814 A1 | 7/2005 | Karahalios | |
| 2005/0161120 A1 | 7/2005 | Inagaki et al. | |
| 2005/0165483 A1 | 7/2005 | Ray et al. | |
| 2005/0203630 A1 | 9/2005 | Pope et al. | |
| 2005/0251257 A1 | 11/2005 | Mitchell et al. | |
| 2006/0041313 A1 | 2/2006 | Allard et al. | |
| 2006/0093646 A1 | 5/2006 | Cima et al. | |
| 2006/0100705 A1 | 5/2006 | Puno et al. | |
| 2006/0122701 A1* | 6/2006 | Kiester | A61F 2/447 623/17.11 |
| 2006/0149372 A1 | 7/2006 | Paxson et al. | |
| 2006/0149376 A1 | 7/2006 | Shimp et al. | |
| 2006/0167549 A1 | 7/2006 | Mathys et al. | |
| 2006/0190079 A1 | 8/2006 | Istephanous et al. | |
| 2006/0219661 A1 | 10/2006 | Towse et al. | |
| 2006/0235534 A1 | 10/2006 | Gertzman et al. | |
| 2006/0265065 A1 | 11/2006 | Bagga et al. | |
| 2006/0293748 A1 | 12/2006 | Alexander et al. | |
| 2007/0010885 A1 | 1/2007 | Liu et al. | |
| 2007/0093898 A1 | 4/2007 | Schwab et al. | |
| 2007/0118220 A1 | 5/2007 | Liu et al. | |
| 2007/0118223 A1 | 5/2007 | Allard et al. | |
| 2007/0233247 A1 | 10/2007 | Schwab | |
| 2007/0233248 A1 | 10/2007 | Schwab et al. | |
| 2007/0260320 A1 | 11/2007 | Peterman et al. | |
| 2007/0269475 A1 | 11/2007 | Gil et al. | |
| 2007/0270951 A1 | 11/2007 | Davis et al. | |
| 2007/0270956 A1 | 11/2007 | Heinz | |
| 2007/0270961 A1* | 11/2007 | Ferguson | A61F 2/44 623/17.11 |
| 2007/0270968 A1* | 11/2007 | Baynham | A61F 2/447 623/17.11 |
| 2007/0282441 A1 | 12/2007 | Stream et al. | |
| 2007/0288028 A1 | 12/2007 | Gorensek et al. | |
| 2007/0293949 A1 | 12/2007 | Salerni et al. | |
| 2008/0014243 A1 | 1/2008 | Ellingsen et al. | |
| 2008/0071380 A1 | 3/2008 | Sweeney | |
| 2008/0077171 A1 | 3/2008 | Blain et al. | |
| 2008/0097610 A1 | 4/2008 | Guyer et al. | |
| 2008/0154378 A1 | 6/2008 | Pelo | |
| 2008/0195209 A1 | 8/2008 | Garcia et al. | |
| 2008/0221689 A1 | 9/2008 | Chaput et al. | |
| 2008/0249622 A1 | 10/2008 | Gray | |
| 2008/0269764 A1 | 10/2008 | Blain et al. | |
| 2008/0269806 A1 | 10/2008 | Zhang et al. | |
| 2008/0288076 A1 | 11/2008 | Soo et al. | |
| 2009/0005784 A1 | 1/2009 | Blain et al. | |
| 2009/0005871 A1 | 1/2009 | White et al. | |
| 2009/0014243 A1 | 1/2009 | Whigham | |
| 2009/0024132 A1 | 1/2009 | Blain et al. | |
| 2009/0082819 A1 | 3/2009 | Blain et al. | |
| 2009/0088800 A1 | 4/2009 | Blain et al. | |
| 2009/0088853 A1 | 4/2009 | Ogilvie et al. | |
| 2009/0132048 A1 | 5/2009 | Denzer | |
| 2009/0182432 A1 | 7/2009 | Zdeblick et al. | |
| 2009/0187247 A1 | 7/2009 | Metcalf, Jr. et al. | |
| 2009/0204152 A1 | 8/2009 | Blain | |
| 2009/0234362 A1 | 9/2009 | Blain et al. | |
| 2009/0264928 A1 | 10/2009 | Blain | |
| 2009/0276049 A1 | 11/2009 | Weiland | |
| 2009/0312837 A1 | 12/2009 | Eisermann et al. | |
| 2010/0023057 A1 | 1/2010 | Aeschlimann | |
| 2010/0036496 A1* | 2/2010 | Yu | A61F 2/4425 623/17.14 |
| 2010/0076559 A1 | 3/2010 | Bagga et al. | |
| 2010/0094426 A1 | 4/2010 | Grohowski, Jr. et al. | |
| 2010/0121385 A1 | 5/2010 | Blain et al. | |
| 2010/0137989 A1* | 6/2010 | Armstrong | A61F 2/4465 623/17.16 |
| 2010/0173264 A1 | 7/2010 | Fredriksson et al. | |
| 2010/0204798 A1 | 8/2010 | Gerbec et al. | |
| 2010/0218854 A1 | 9/2010 | Garcia Saban et al. | |
| 2010/0228288 A1 | 9/2010 | Blain | |
| 2010/0234958 A1 | 9/2010 | Linares | |
| 2010/0249937 A1 | 9/2010 | Blain et al. | |
| 2010/0274286 A1 | 10/2010 | Blain et al. | |
| 2010/0274358 A1 | 10/2010 | Mueller et al. | |
| 2010/0303722 A1 | 12/2010 | Jin et al. | |
| 2011/0009965 A1 | 1/2011 | Ankem | |
| 2011/0040301 A1 | 2/2011 | Blain et al. | |
| 2011/0082503 A1 | 4/2011 | Blain | |
| 2011/0190902 A1 | 8/2011 | Tong et al. | |
| 2011/0224796 A1 | 9/2011 | Weiland et al. | |
| 2011/0230970 A1 | 9/2011 | Lynn et al. | |
| 2011/0230971 A1* | 9/2011 | Donner | A61B 17/70 623/17.16 |
| 2011/0233169 A1 | 9/2011 | Mayfield et al. | |
| 2011/0282454 A1 | 11/2011 | Ullrich, Jr. et al. | |
| 2012/0009341 A1 | 1/2012 | Noh et al. | |
| 2012/0046695 A9 | 2/2012 | Blain | |
| 2012/0078371 A1* | 3/2012 | Gamache | A61F 2/4465 623/17.16 |
| 2012/0123424 A1 | 5/2012 | Blain et al. | |
| 2012/0123548 A1 | 5/2012 | Lynn et al. | |
| 2012/0136443 A1 | 5/2012 | Wenzel | |
| 2012/0149991 A1 | 6/2012 | Blain et al. | |
| 2012/0158056 A1 | 6/2012 | Blain | |
| 2012/0158144 A1 | 6/2012 | Ullrich, Jr. et al. | |

(56) References Cited

U.S. PATENT DOCUMENTS

| | | |
|---|---|---|
| 2012/0172991 A1 | 7/2012 | Bertele et al. |
| 2012/0226357 A1 | 9/2012 | Varela |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2386274 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Pending U.S. Appl. No. 13/286,813 of Chad J. Patterson, et al. filed Nov. 1, 2011.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

Pending U.S. Appl. No. 13/826,304 of Peter F. Ullrich, Jr., et al. filed Mar. 14, 2013.

Supplementary Partial European Search Report issued Aug. 19, 2011, for EP 06 75 9086.

Supplementary Partial European Search Report issued Sep. 27, 2011, for EP 06 75 9086.

Variola, et al., "Nanoscale surface modifications of medically relevant metals: state-of-the art and prespectives", Nanoscale, 2011, 3, 335-353.

Wennerberg, A., et al., "Effects of titanium surface topography on bone integration: a systematic review", Clin. Oral Impl. Res., 20 (Suppl. 4), 2009, pp. 172-184.

Wennerberg, et al., "Spontaneously formed nanostructures on titanium surfaces", Clin. Oral Impl. Res., 2012, 1-7.

* cited by examiner

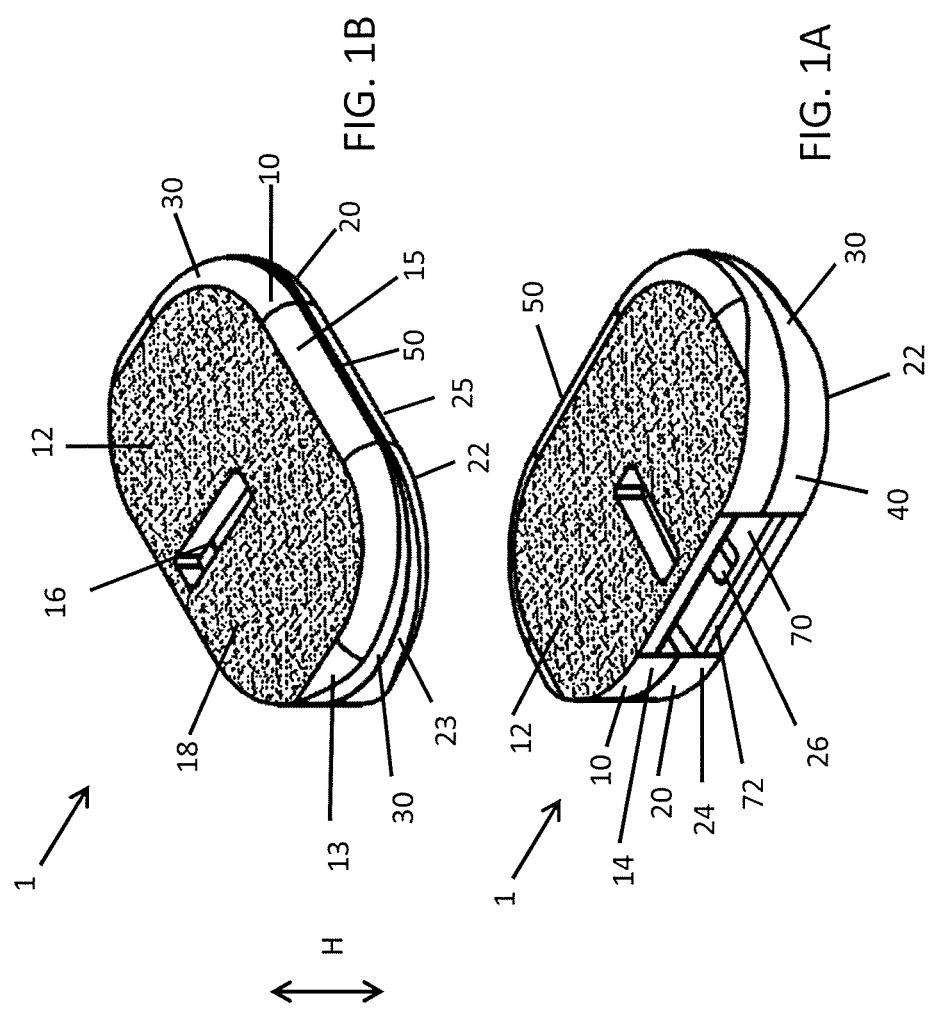

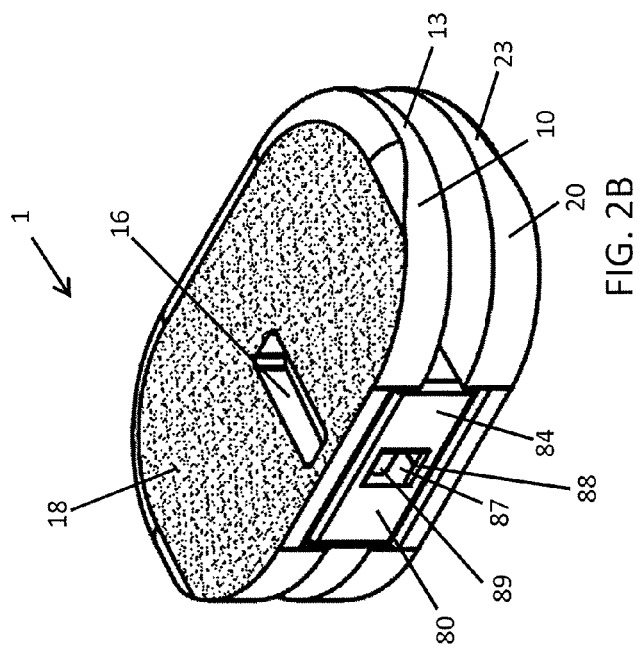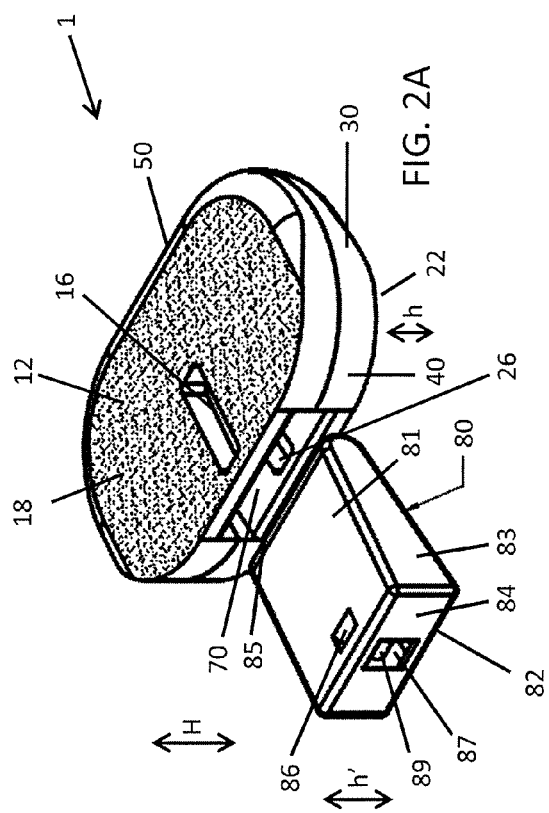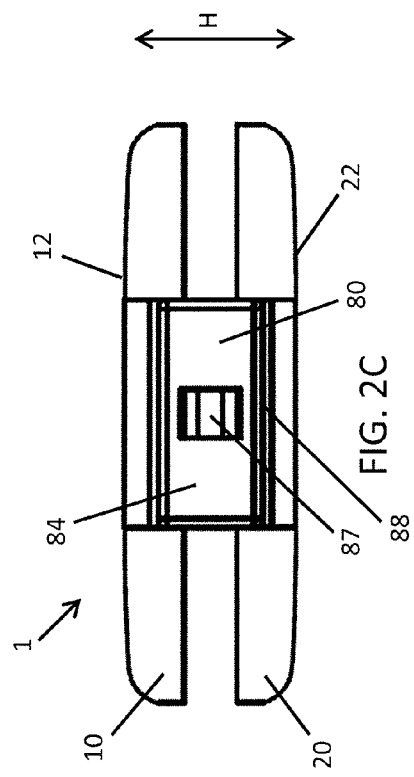

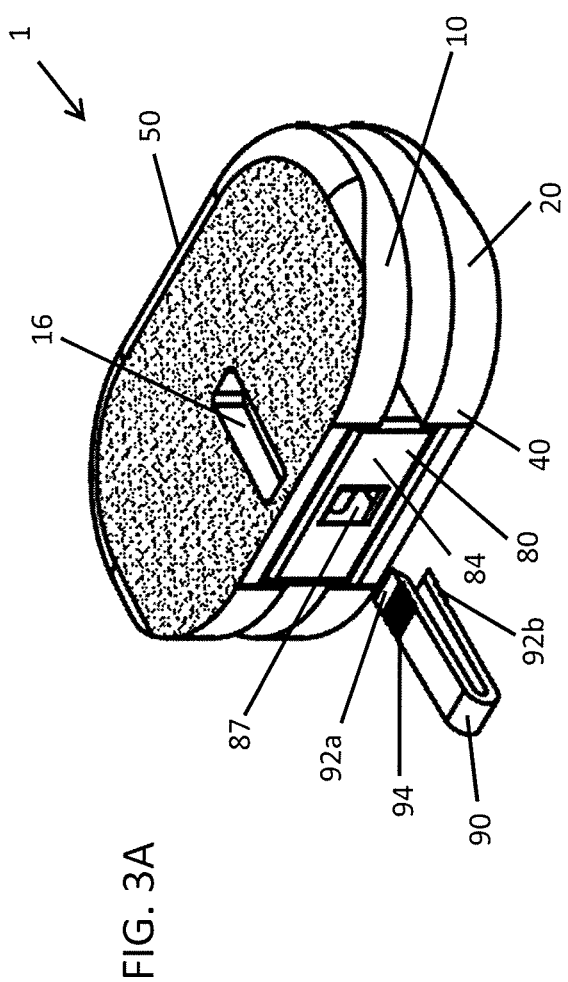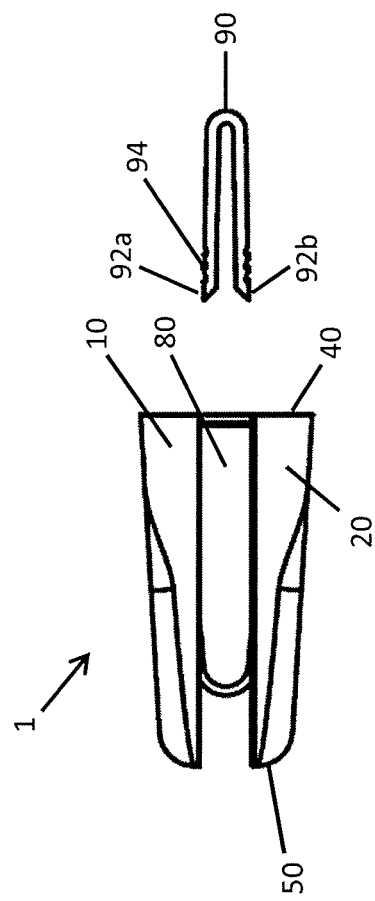
FIG. 3A
FIG. 3B

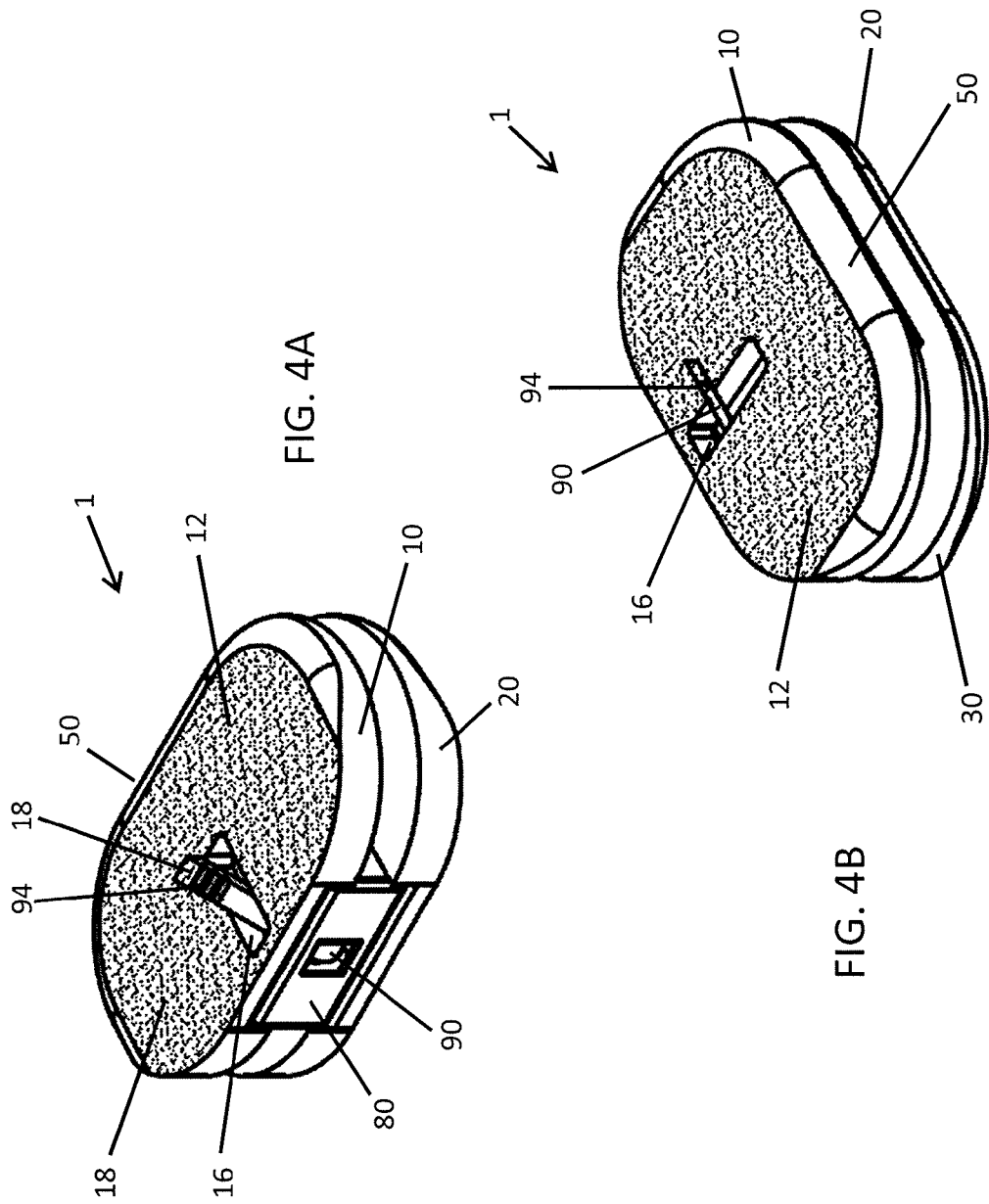

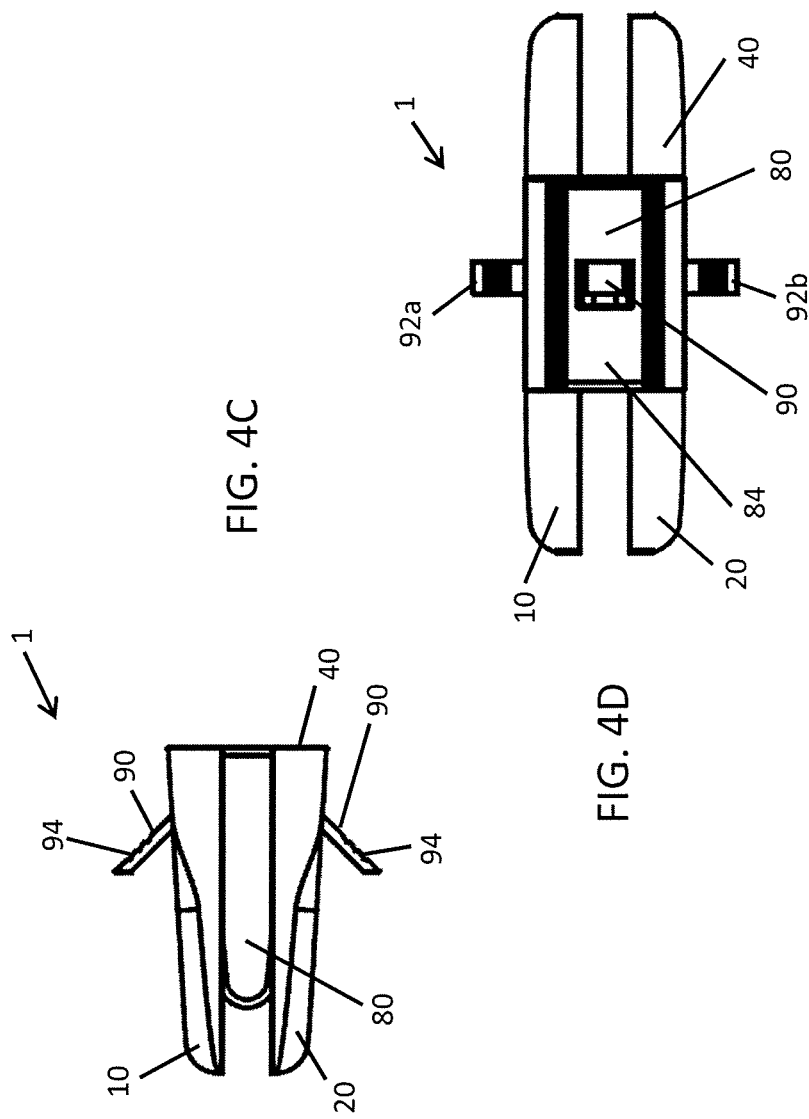

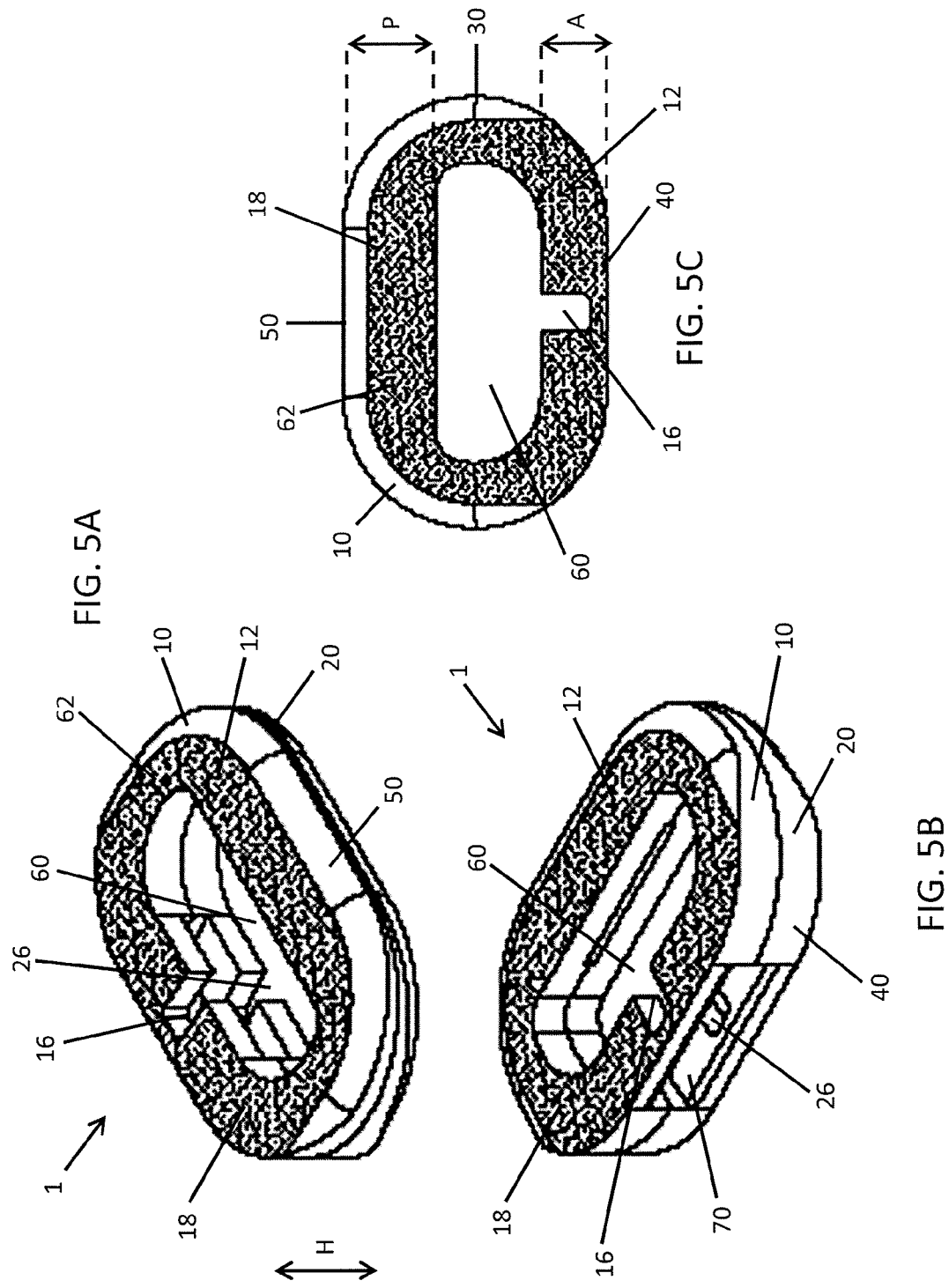

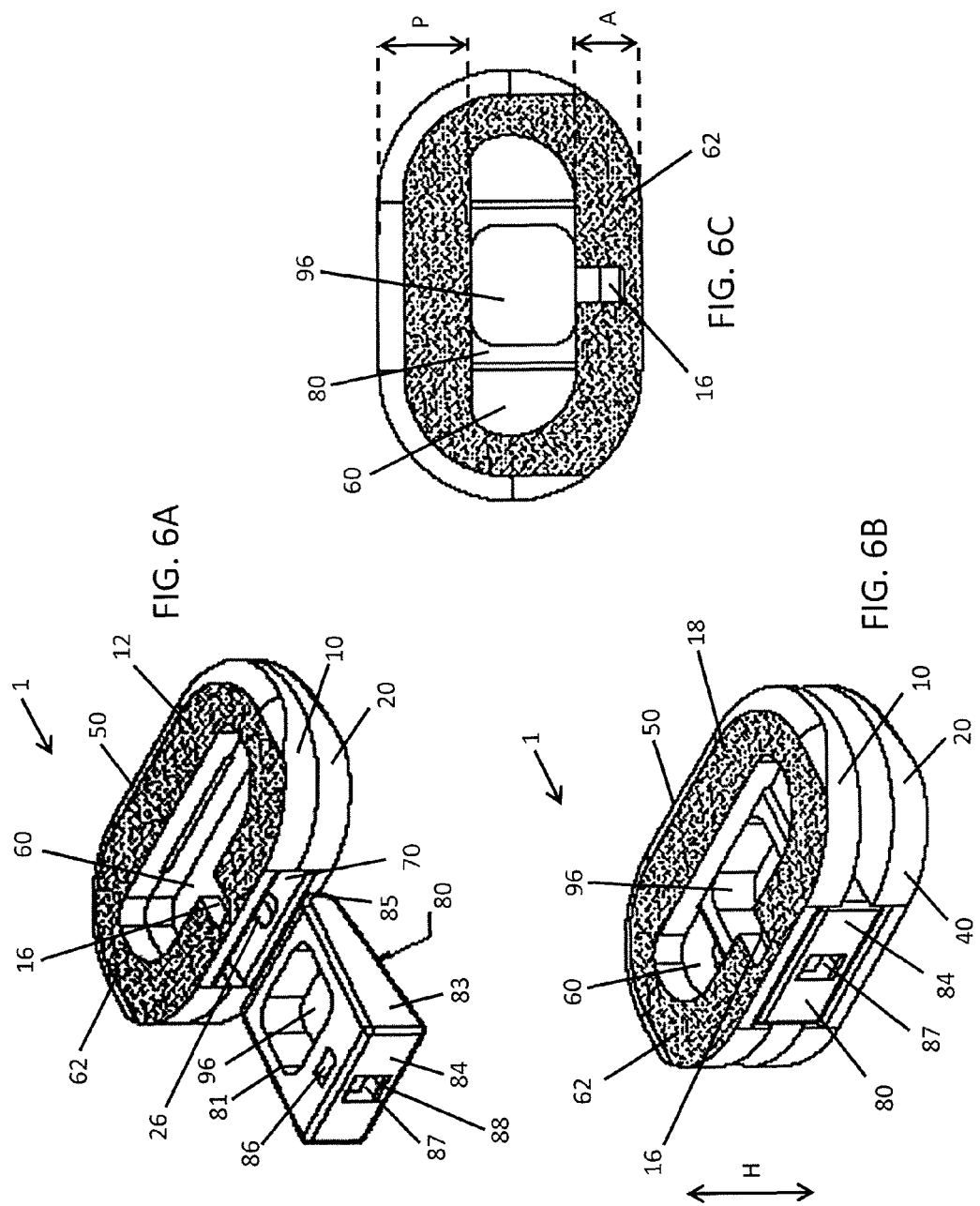

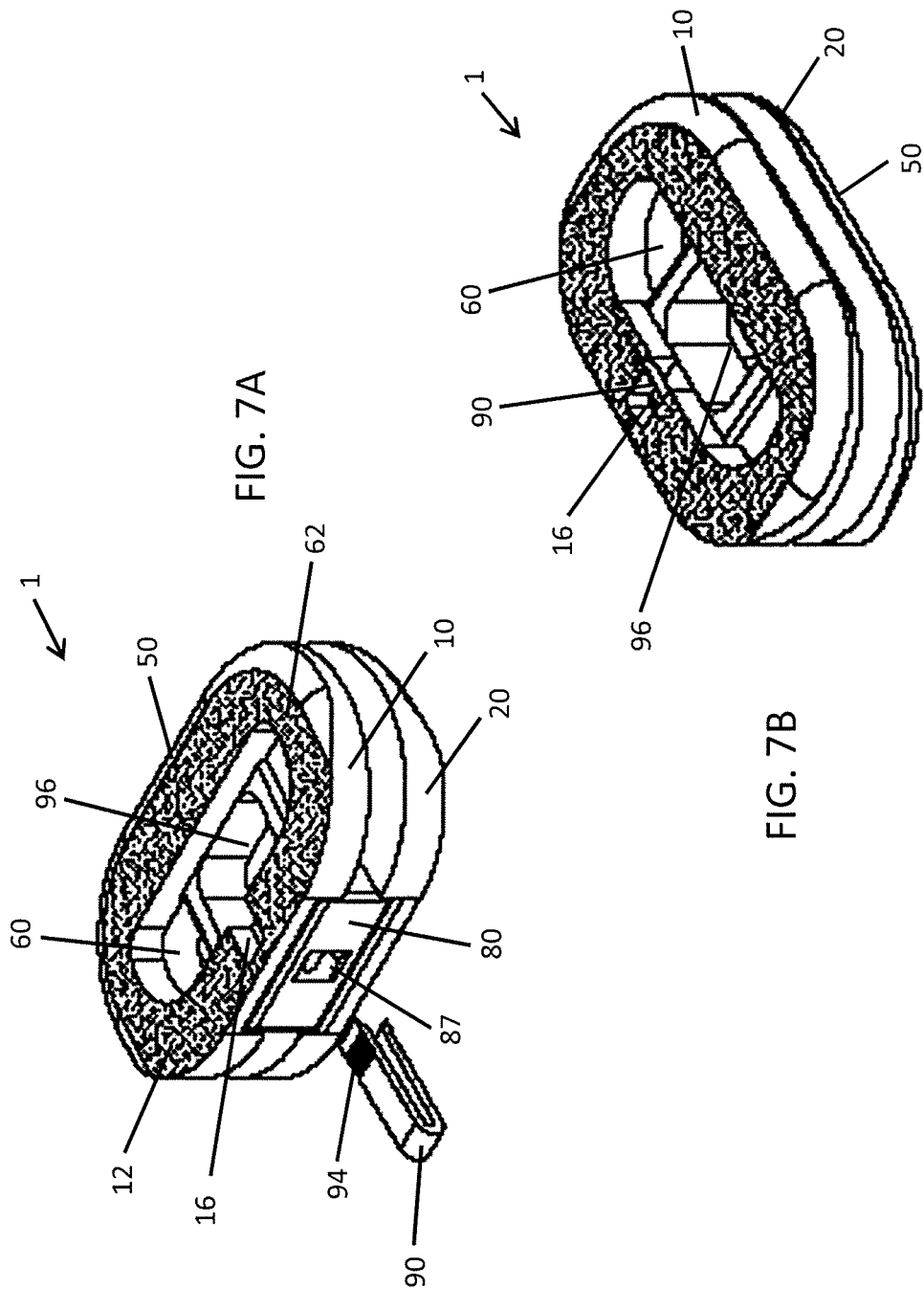

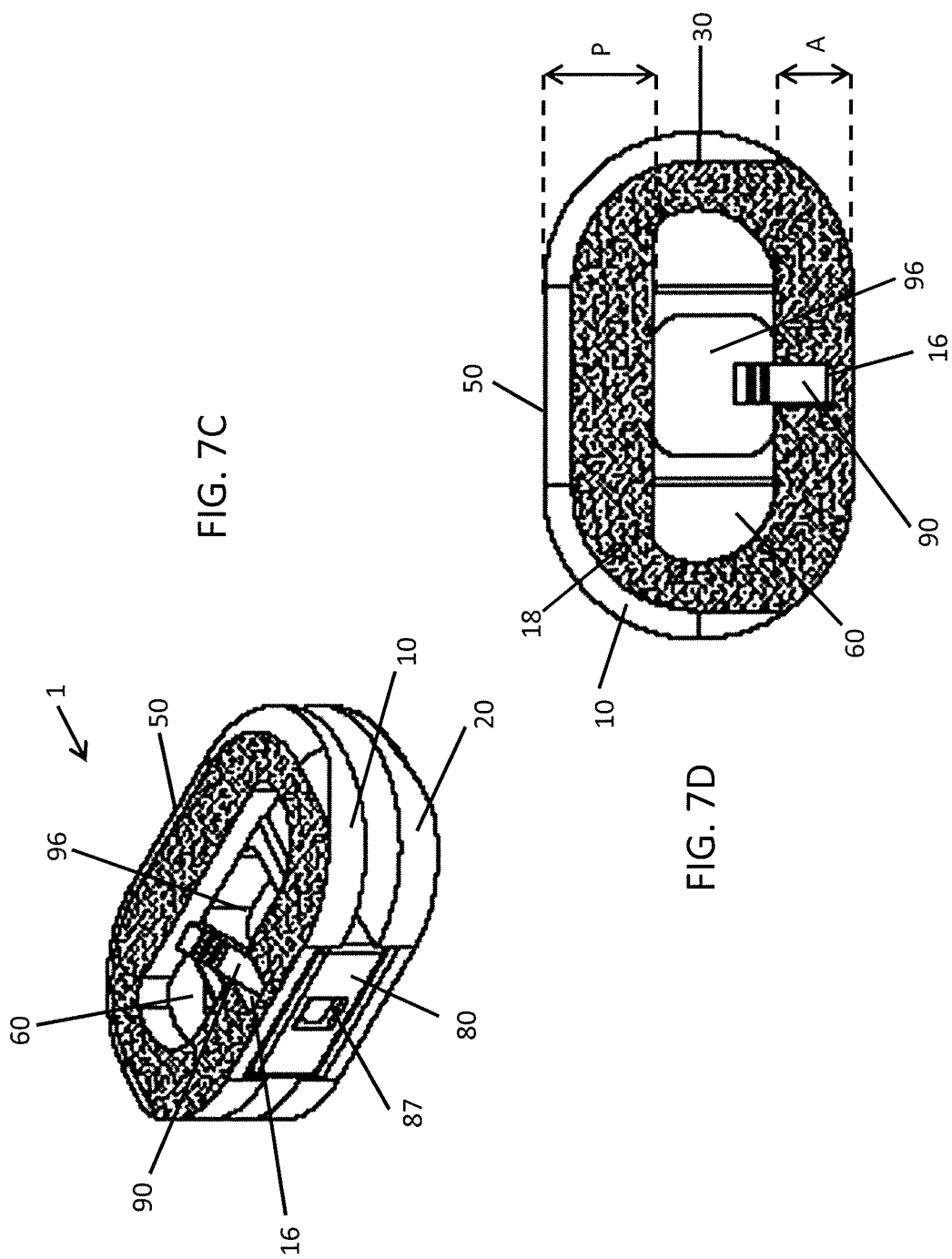

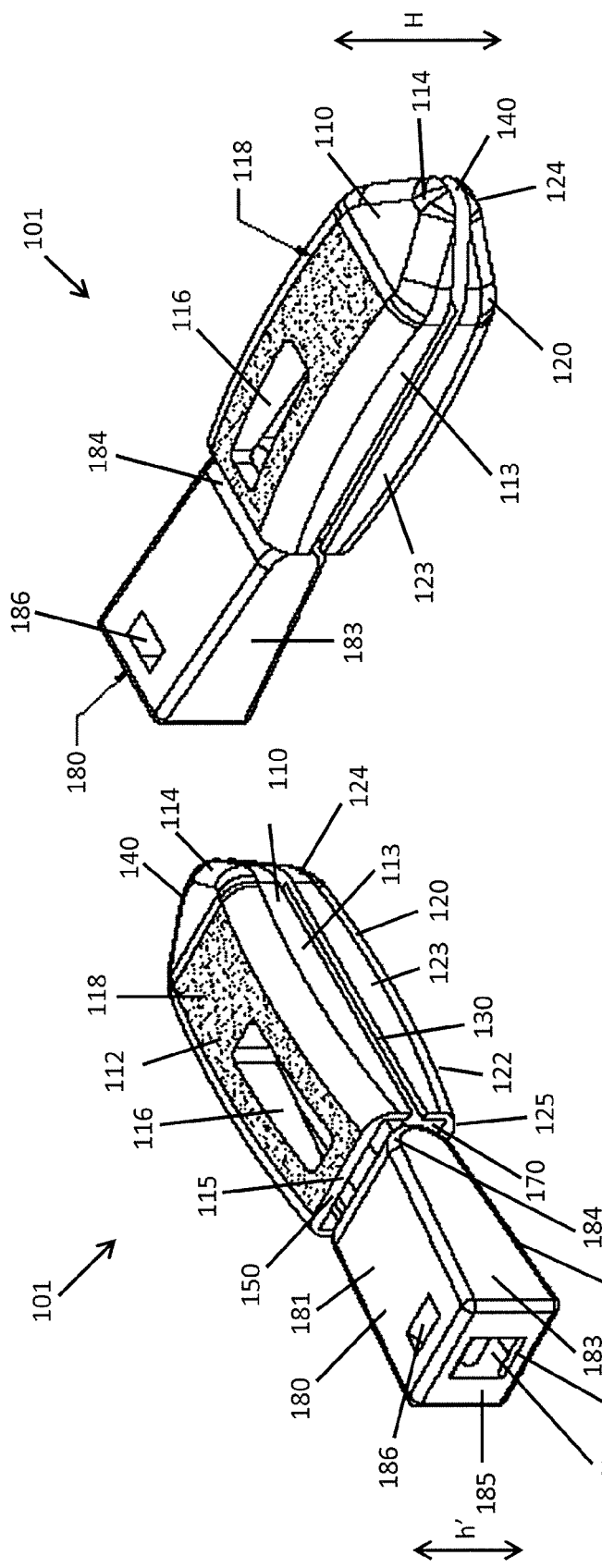

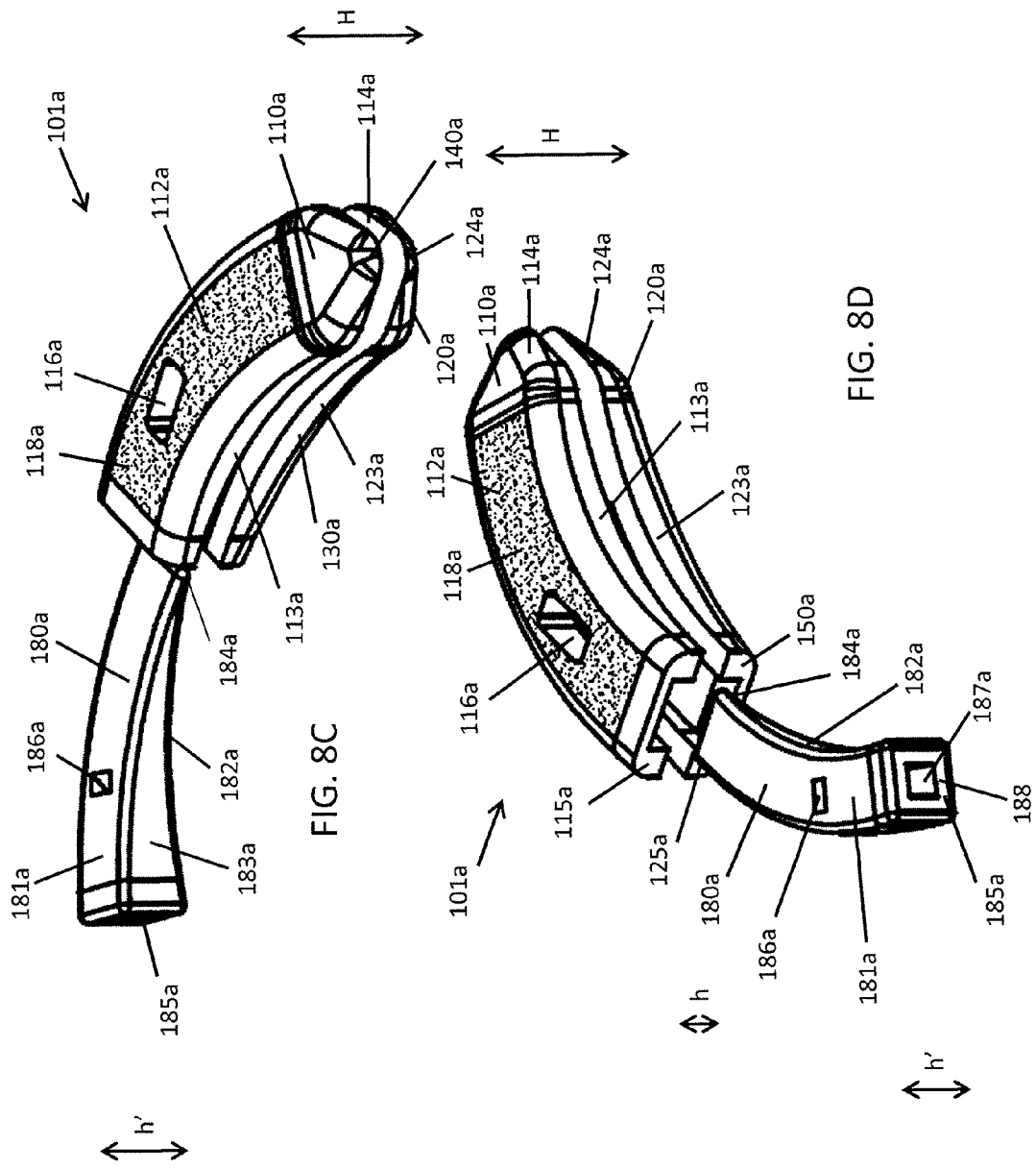

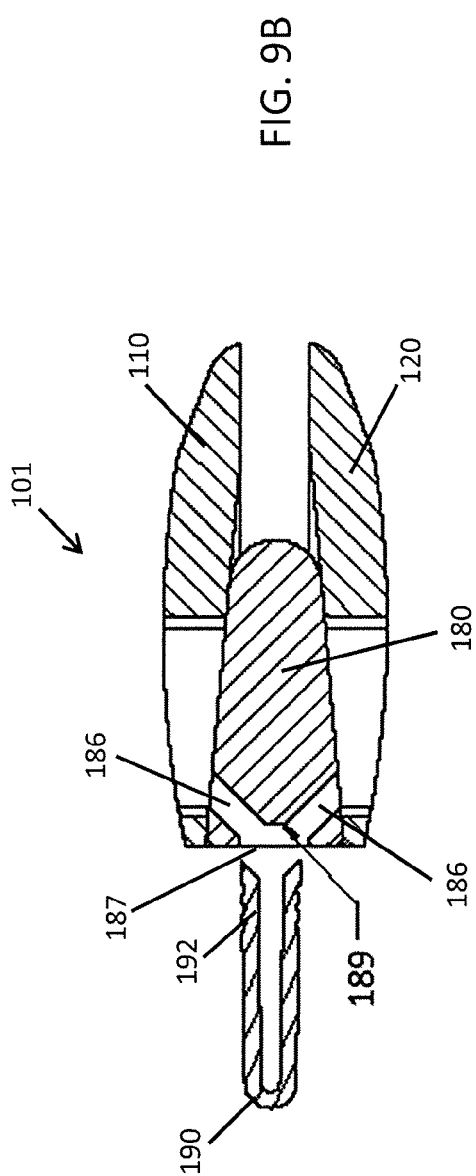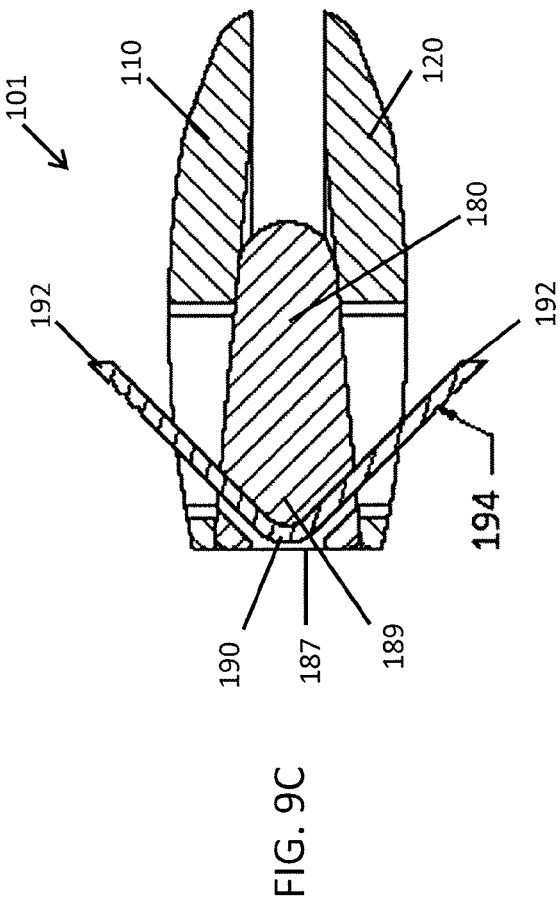

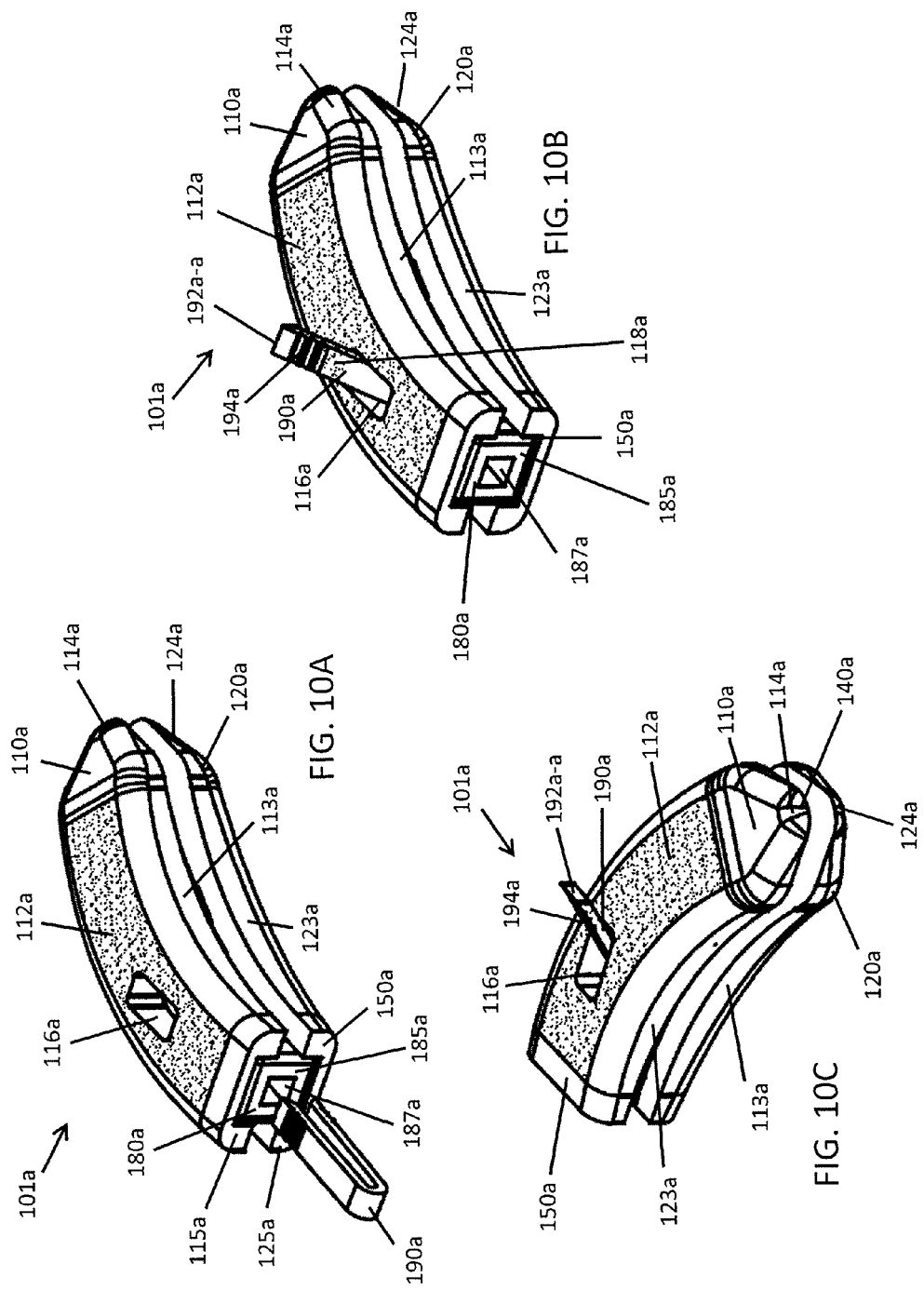

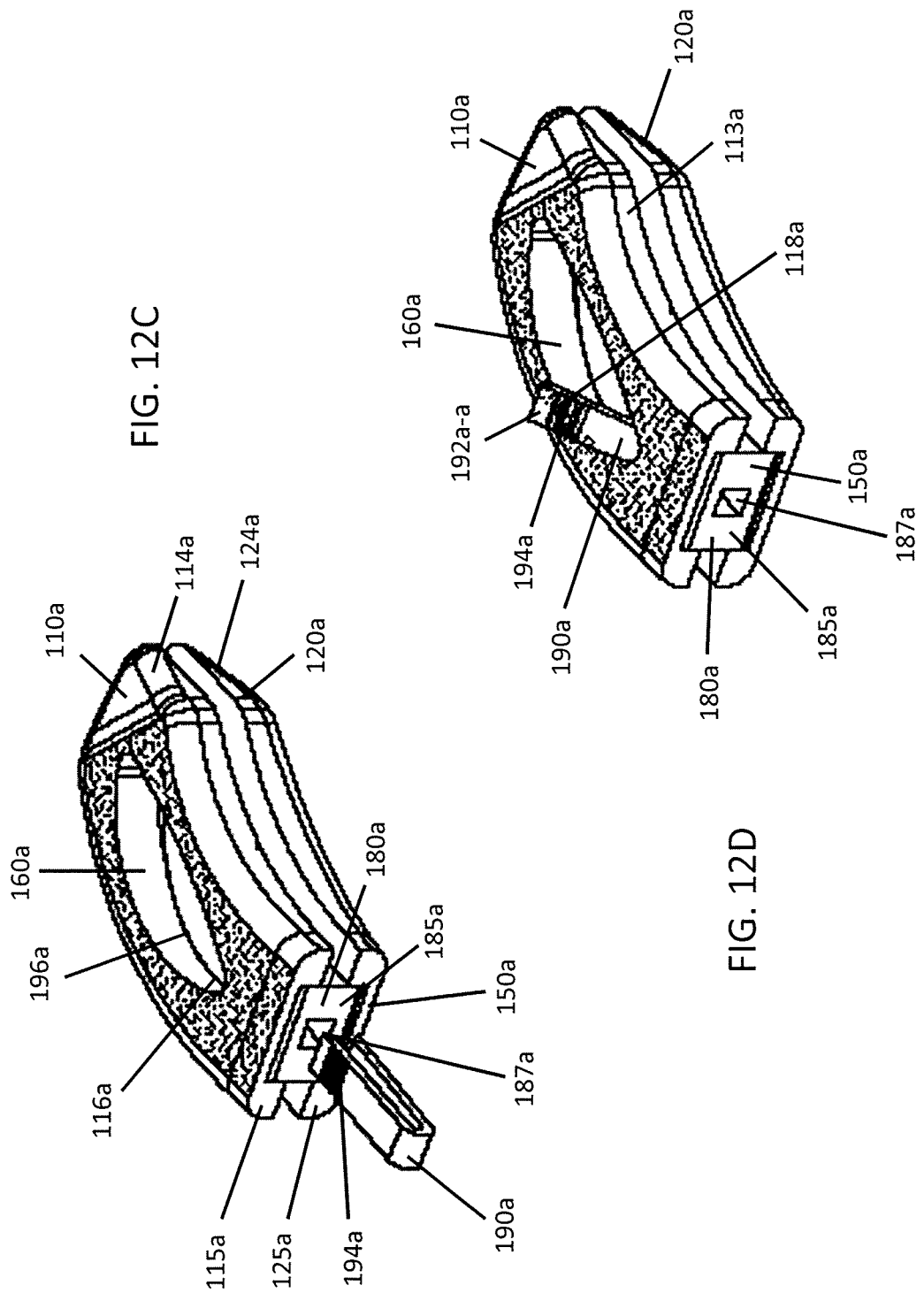

EXPANDABLE SPINAL IMPLANT WITH EXPANSION WEDGE AND ANCHOR

CROSS REFERENCE TO RELATED APPLICATIONS

This application claims priority to U.S. Provisional Application No. 61/711,403, filed on Oct. 9, 2012, the contents of which are incorporated by reference herein, in their entirety and for all purposes.

FIELD OF THE INVENTION

The invention relates generally to expandable interbody spinal implants, into which an expansion wedge may be inserted to increase the implant height, and methods of using such implants in spinal fusion applications.

BACKGROUND OF THE INVENTION

Various publications, including patents, published applications, technical articles and scholarly articles are cited throughout the specification. Each of these cited publications is incorporated by reference herein, in its entirety and for all purposes.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Nevertheless, traditional implantation practices often do not preserve critical bone structures such as vertebral endplates during the surgical procedure. In some cases, the implant devices themselves necessitate removal of bone and were not designed or implanted with the intent to preserve critical bone structures during or after implantation.

In addition, traditional implantation procedures require an incision large enough to fit the full implant through, and require sufficient dissection of internal tissues in order to provide a clear pathway from the incision to the implantation locus. The incision and dissection necessarily cause tissue trauma, tend to increase pain and discomfort, and prolong recovery time in the patient, and also may increase the chances of a complication to the patient resulting from the implantation procedure. Accordingly, there is a standing need to reduce tissue trauma in implantation patients. It is a general desire to reduce the size of the implant such that the incision and tissue dissection can be minimized, yet any reduction in size must be balanced with the need for the implant to adequately stand in the place of the tissue it replaces. In other words, an implant that is smaller must still be able to adequately bear the load in the body.

SUMMARY OF THE INVENTION

The invention features interbody spinal implants and systems. In some aspects, the implant comprises a top portion comprising an anterior face, a posterior face, opposing lateral sides, and a top surface comprising a roughened surface topography adapted to grip bone and inhibit migration of the implant, and a slot for receiving a prong of an anchor pin extending through the top portion, and a bottom portion separate from the top portion, the bottom portion comprising an anterior face, a posterior face, opposing lateral sides, and a bottom surface comprising a roughened surface topography adapted to grip bone and inhibit migration of the implant, and a slot for receiving a prong of an anchor pin extending through the bottom portion. A moveable joint preferably connects the top portion and bottom portion together, and allows the top and bottom portions to move vertically relative to each other. The implant comprises a socket for receiving an expansion wedge, with an opening to access the socket on either the anterior or posterior face of the top and bottom portions. Since the implant comprises top and bottom portions, each such portion comprises a portion of the socket, and this portion of the socket may be equal in each of the top and bottom portions, or may be unequal with more or less of the socket in either the top or bottom portions. The implant may be used, for example, to repair defective or damaged intervertebral disks in the spinal column, including cervical, thoracic, or lumbar disks.

A system may comprise the implant. The system also comprises an expansion wedge comprising a top surface, a bottom surface, an anterior face, a posterior face, opposing lateral sides, and an opening on either the anterior face or posterior face for receiving an anchor pin, the opening in communication with a first channel extending through the top surface of the wedge and a second channel extending through the bottom surface of the wedge. The system also comprises an anchor pin comprising at least two prongs comprising a plurality of ridges or teeth. The system may further comprise a bone graft material disposed in the vertical aperture of the implant, including cancellous autograft bone, allograft bone, demineralized bone matrix (DBM), porous synthetic bone graft substitute, bone morphogenic protein (BMP), or a combination thereof.

The top portion and the bottom portion of the implant may further comprise a vertical aperture extending from the top surface through the bottom surface of the implant. In the system, the expansion wedge may further comprise a vertical aperture extending from the top surface of the wedge to the bottom surface of the wedge.

The implant may be generally oval-shaped in transverse cross-section. The implant may be generally rectangular-shaped in transverse cross-section. The implant may have a curved rectangular cross-section. The expansion wedge may comprise substantially the same shape in cross-section as the implant into which it will be inserted.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1A shows an anterior perspective of an expandable implant;

FIG. 1B shows a posterior perspective of an expandable implant;

FIG. 2A shows an anterior perspective of an expandable implant and an expansion wedge positioned for insertion into the implant;

FIG. 2B shows an anterior perspective of an expandable implant with the expansion wedge inserted into the socket, and with the top and bottom halves of the implant body separated;

FIG. 2C shows a perspective of the top and bottom halves of the implant body pushed apart due to the presence of the inserted expansion wedge;

FIG. 3A shows an anterior perspective of an expandable implant with the expansion wedge inserted into the socket, and an anchor pin positioned for insertion into the expansion wedge;

FIG. 3B shows a lateral view of the expandable implant and anchor pin;

FIG. 4A shows an anterior perspective of an expandable implant with the expansion wedge inserted into the socket, and the anchor pin inserted into the expansion wedge, with the prongs of the anchor pin extending out from the top surface of the implant;

FIG. 4B shows a posterior perspective of an expandable implant with the expansion wedge inserted into the socket, and the anchor pin inserted into the expansion wedge, with the prongs of the anchor pin extending out from the top surface of the implant;

FIG. 4C shows a lateral view of the expandable implant and extended anchor pin prongs;

FIG. 4D shows an anterior view of the expandable implant and extended anchor pin prongs;

FIG. 5A shows a posterior perspective of an expandable implant having a vertical aperture and an anchor pin slot through the top and bottom sections;

FIG. 5B shows an anterior perspective of an expandable implant having a vertical aperture and an anchor pin slot through the top and bottom sections;

FIG. 5C shows a top perspective of the vertical aperture and anchor pin slot;

FIG. 6A shows an anterior perspective of an expandable implant and an expansion wedge, each having a vertical aperture and anchor pin slot;

FIG. 6B shows an anterior perspective of an expandable implant with an inserted expansion wedge, each having a vertical aperture and anchor pin slot;

FIG. 6C shows a top perspective of the implant and expansion wedge vertical apertures when aligned;

FIG. 7A shows an anterior perspective of an expandable implant and expansion wedge, each having a vertical aperture and anchor pin slot, with an anchor pin positioned for insertion;

FIG. 7B shows a posterior perspective of an expandable implant and expansion wedge, with aligned vertical apertures, and with an anchor pin extending out from the anchor pin slot;

FIG. 7C shows an anterior perspective of an expandable implant and expansion wedge, with aligned vertical apertures, and with an anchor pin extending out from the anchor pin slot;

FIG. 7D shows a top perspective of the implant and expansion wedge vertical apertures when aligned, with an anchor pin extending out from the anchor pin slot;

FIG. 8A shows a posterior perspective of an embodiment of a PLIF expandable implant and expansion wedge positioned for insertion;

FIG. 8B shows an anterior perspective of an embodiment of a PLIF expandable implant and expansion wedge positioned for insertion;

FIG. 8C shows an anterior perspective of a curved embodiment of a PLIF expandable implant, with a curved embodiment of an expansion wedge positioned for insertion;

FIG. 8D shows a posterior perspective of a curved embodiment of a PLIF expandable implant, with a curved embodiment of an expansion wedge positioned for insertion;

FIG. 9B shows a cut-away view of an embodiment of a PLIF expandable implant, illustrating the deflection spur and channels for each prong of the anchor pin;

FIG. 9C shows a cut-away view of an embodiment of a PLIF expandable implant with an anchor pin extending through each channel, with the ends of the anchor pin prongs extending out from the top and bottom surface of the implant;

FIG. 10A shows a posterior perspective an embodiment of a curved PLIF expandable implant with an expansion wedge inserted and with the anchor pin aligned for insertion into the expansion wedge;

FIG. 10B shows a posterior perspective of an embodiment of a curved PLIF expandable implant with an expansion wedge inserted, and an anchor pin secured in place;

FIG. 10C shows an anterior perspective of an embodiment of a curved PLIF expandable implant with an expansion wedge inserted, and an anchor pin secured in place;

FIG. 12C shows a posterior perspective of an embodiment of a curved PLIF expandable implant having a vertical aperture, with the expansion wedge having a vertical aperture inserted into the implant and an anchor pin aligned for insertion; and FIG. 12D shows a posterior perspective of an embodiment of a curved PLIF expandable implant having a vertical aperture, with the expansion wedge having a vertical aperture inserted into the implant and an anchor pin secured in place.

DETAILED DESCRIPTION OF THE INVENTION

Figure 9A:
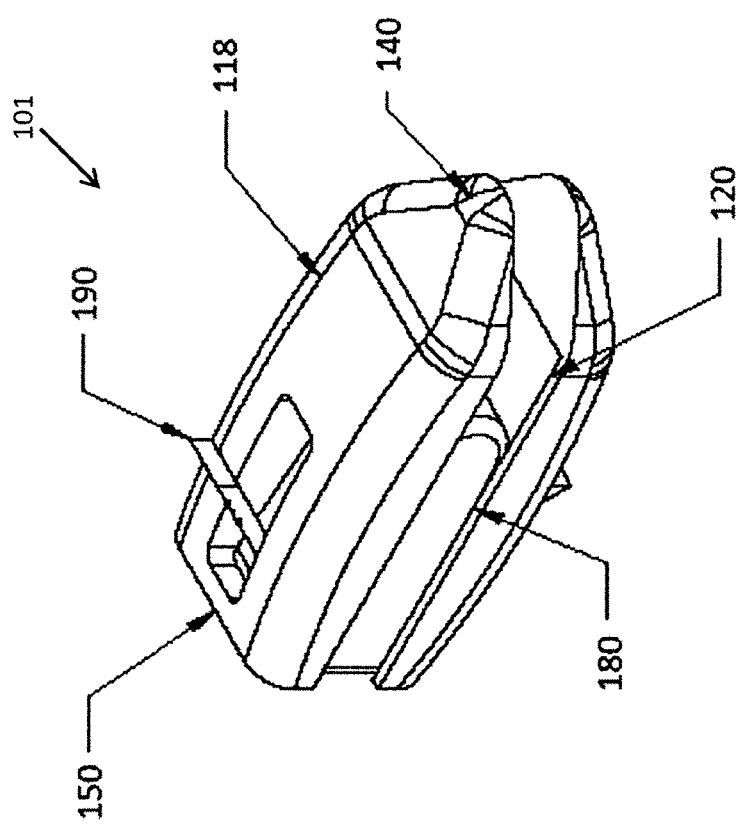
FIG. 9A shows an embodiment of a PLIF expandable implant with the expansion wedge inserted and the anchor pin secured, and with the top and bottom portions of the implant spaced apart.

The invention features interbody spinal implants comprising self-deploying anchors. The implant is adaptable to different conditions between vertebrae, and helps to stabilize the implant, while preserving vertebral endplate bone. Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

Interbody spinal implants, expansion wedges, and anchor pins that are described below and in accordance with the invention are preferably made of a durable material such as stainless steel, stainless steel alloy, titanium, or titanium alloy, but can also be made of other durable materials such as, but not limited to, polymeric, ceramic, and composite materials. For example, certain embodiments of the interbody spinal implants, expansion wedges, and anchor pins may be comprised of a biocompatible, polymeric matrix reinforced with bioactive fillers, fibers, or both. Certain embodiments of the interbody spinal implants, expansion wedges, and anchor pins may be comprised of urethane dimethacrylate (DUDMA)/tri-ethylene glycol dimethacrylate (TEDGMA) blended resin and a plurality of fillers and fibers including bioactive fillers and E-glass fibers. Durable materials also include any number of pure metals, metal alloys, or both. Titanium and its alloys are generally preferred for certain embodiments due to their acceptable, and desirable, strength and biocompatibility. In this manner, certain embodiments of the interbody spinal implants, expansion wedges, and anchor pins may have improved structural integrity and may better resist fracture during implantation by impact. Suitable polymeric materials include polyetherether-ketone, hedrocel, and ultra-high molecular weight polyethylene. Composites may include a combination of metals and polymeric materials.

Referring now to the drawing, in which like reference numbers refer to like elements throughout the various figures that comprise the drawing, FIG. 1A and FIG. 1B show a first embodiment of an interbody spinal implant 1 especially well-adapted for use in an ALIF procedure. The implant 1 is comprised of two primary sections, a top portion 10 and a bottom portion 20. The top portion 10 comprises a top surface 12, and the bottom portion 20 comprises a bottom surface 22. The top portion 10 and bottom portion 20 preferably are not directly connected to each other such that they may be separated when the implant 1 expands, as detailed below. The top portion 10 and bottom portion 20 may be indirectly connected to each other through at least one movable joint (not shown) that holds these portions together to form the implant 1. When the implant 1 is not expanded, the at least one movable joint is/are substantially closed such that the top portion 10 and bottom portion 20 may contact each other or at least be in close proximity to each other, as shown in FIGS. 1A and 1B. When the implant expands, the at least one movable joint opens such that the top portion 10 and bottom portion 20 separate, but do not become detached from the implant 1. The movable joint is operably connected to each of the top portion 10 and bottom portion 20. One or more of the top surface 12 and the bottom surface 22 comprises a roughened topography 18.

The top portion 10 comprises an anterior side 14, a posterior side 15, and opposing lateral sides 13. The bottom portion 20 comprises an anterior side 24, a posterior side 25, and opposing lateral sides 23. The anterior sides 14 and 24 together comprise an anterior face 40 of the implant 1. The posterior sides 15 and 25 together comprise a posterior face 50 of the implant 1. The opposing lateral sides 13 and 23 together comprise opposing lateral faces 30 of the implant 1. In some aspects, the interbody spinal implant 1 has a generally oval-shaped transverse cross-section, with smooth, blunted, or rounded opposing lateral faces 30 and a smooth, blunted, or rounded posterior face 50.

In preferred aspects, the implant 1 comprises a socket 70, with an opening 74 to the socket 70 on the anterior face 40 (FIG. 1A). The socket 70 receives an expansion wedge 80 (FIG. 2A). The opening 74 is comprised of a section of each of the anterior sides 14 and 24. In some aspects, the socket 70 is configured or includes one or more engagement structures 72 to facilitate insertion and placement of the implant 1 by the practitioner during an implant procedure. For example, such configurations or engagement structures 72 may receive and engage a surgical tool, and the surgical tool may be used to move the implant 1 about the intervertebral space. The engagement structures 72 may comprise screw threads 72, ribs 72, one or more notches 72, one or more lips 72, ridges 72, flanges 72, barbs 72, grooves 72, or any combination thereof, to enhance engagement with a surgical tool to reduce the possibility of the surgical tool slipping out of the engagement structures 72. The top portion 10 and the bottom portion 20 of the implant 1 each preferably comprise a slot 16 (top portion), 26 (bottom portion) near the anterior side 14 or 24, and extending from the top surface 12 and through the top portion 10, and extending from the bottom surface 22 and through the bottom portion 20, and into the socket 70 (FIG. 1A and FIG. 1B).

An expansion wedge 80 is inserted into the opening 74 and advanced into the socket 70 (FIG. 2A and FIG. 2B). The expansion wedge 80 comprises a top surface 81, a bottom surface 82, opposing lateral sides 83, an anterior face 84, and a posterior face 85. Generally, the posterior face 85 is the section that is first inserted into the opening 74.

The expansion wedge 80 comprises at least one channel 86 on each of the top 81 and bottom surfaces 82. The expansion wedge 80 also comprises at least one opening 87 on the anterior face 84. The opening 87 is preferably in communication with each channel 86. The opening 87 preferably receives the prongs 92 of an anchor pin 90 (FIG. 3A and FIG. 3B). The opening 87 may comprise one or more engagement structures 88 to facilitate insertion and placement of the expansion wedge 80 into the socket 70 of the implant, and/or insertion and placement of the implant 1 by the practitioner during an implant procedure. The engagement structures 88 may comprise screw threads 88, ribs 88, one or more notches 88, one or more lips 88, ridges 88, flanges 88, barbs 88, grooves 88, or any combination thereof. The engagement structures 88 may receive and engage a surgical tool, and the surgical tool may be used to move the implant 1 about the intervertebral space. For example, once the expansion wedge 80 is fully inserted into the socket 70 (FIG. 2B-FIG. 2D), the engagement structures 72 on the socket 70 may no longer be fully accessible such that the engagement structures 88 of the wedge 80 stand in the place of the engagement structures 72 of the socket 70 to allow further manipulation of the implant 1 by surgical tools within the intervertebral space.

The expansion wedge 80 may also comprise a spur 89 that may separate and force the prongs 92 of the anchor pin 90 outward and through each channel 86. The spur 89 is preferably substantially wedge-shaped. As the prongs 92 of the anchor pin 90 are advanced into the wedge 80, they contact the spur 89, and are separated and directed toward and into each channel 86.

The anterior face 84 of the expansion wedge 80 comprises a first height h, and the posterior face 85 of the expansion wedge 80 comprises a second height h' that is preferably less than the first height h. The second height h' allows the posterior face 85 to fit within the opening 74 of the implant 1. The first height h may be about 0.5 mm to about 20 mm, about 1 mm to about 3 mm, about 1 mm to about 5 mm, about 1 mm to about 7 mm, about 1 mm to about 10 mm, about 1 mm to about 12 mm, about 1 mm to about 15 mm, about 1 mm to about 18 mm, about 2 mm to about 4 mm, about 2 mm to about 5 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 20 mm, about 3 mm to about 5 mm, about 3 mm to about 7 mm, about 3 mm to about 10 mm, about 3 mm to about 14 mm, about 3 mm to about 16 mm, about 4 mm to about 6 mm, about 4 mm to about 8 mm, about 4 mm to about 12 mm, about 5 mm to about 10 mm, about 5 mm to about 15 mm, about 5 mm to about 20 mm, about 6 mm to about 8 mm, about 6 mm to about 10 mm, about 8 mm to about 12 mm, about 8 mm to about 15 mm, about 8 mm to about 18 mm, about 10 mm to about 15 mm, about 10 mm to about 20 mm, or about 15 mm to about 18 mm. The second height h' may be about 0.5 mm to about 15 mm, about 1 mm to about 3 mm, about 1 mm to about 5 mm, about 1 mm to about 7 mm, about 1 mm to about 10 mm, about 1 mm to about 12 mm, about 1 mm to about 15 mm, about 2 mm to about 4 mm, about 2 mm to about 5 mm, about 2 mm to about 6 mm, about 2 mm to about 8 mm, about 2 mm to about 10 mm, about 2 mm to about 12 mm, about 3 mm to about 5 mm, about 3 mm to about 7 mm, about 3 mm to about 10 mm, about 4 mm to about 6 mm, about 4 mm to about 8 mm, about 4 mm to about 12 mm, about 5 mm to about 10 mm, about 6 mm to about 8 mm, or about 6 mm to about 10 mm. The first height h and second height h' may independently be about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm, about 13 mm, about 14 mm, about 15 mm, about 16 mm, about 17 mm, about 18 mm, about 19 mm, or about 20 mm.

The socket 70 preferably comprises a wedge shape that accommodates the shape of the expansion wedge 80. In this manner, the internal surfaces of the socket 70 contact the top surface 81 and bottom surface 82 of the expansion wedge 80 (e.g., FIG. 9B and FIG. 9C). Thus, for example, when the expansion wedge 80 is fully inserted into the socket 70, the posterior face 85, which has a smaller height (h') than the anterior face 84, maintains contact with a socket surface 70 and does not "float" freely within the center of the implant 1. This helps to ensure that the load is distributed on all surfaces of the expansion wedge 80, without the load being exerted primarily on the highest point of the anterior face 84.

As the expansion wedge 80 is inserted into the socket 70, the implant 1 expands, thereby increasing in height H (FIG. 2B and FIG. 2C). As the expansion wedge 80 advances inward, it forces each of the top portion 10 and bottom portion 20 of the implant 1 apart, thereby increasing the distance between them (FIG. 2C) and increasing the height H. Preferably, the height H increases proportionally with the first height h of the expansion wedge 80. The implant 1 is preferably compatible with expansion wedges 80 having different first heights h and/or second heights h', thereby allowing the implant 1 to be expanded to a desired height H, for example, to accommodate different intervertebral space heights or other conditions of the subject into which the implant 1 is implanted.

Optionally, the expansion wedge 80 may comprise one or more structures to resist expulsion of the wedge 80 from the socket 70 once fully inserted. The structures may comprise a ratchet or tabs (not shown). The expansion wedge 80 may be freely inserted and removed from the socket, and in some aspects does not include any structures to resist expulsion from the socket 70.

The wedge 80 may be fabricated from any suitable materials. The wedge 80 is preferably sufficiently rigid to hold the top 10 and bottom 20 portions of the implant 1 apart and not break under load stress once the implant 1 is implanted. The wedge 80 may be fabricated from a metal, a plastic, a polymer, or a composite, (including any metal, plastic, polymer, or composite described or exemplified herein) and the material is preferably biocompatible.

The anchor pin 90 comprises at least two flexible prongs 92a, 92b preferably spaced apart. Each prong 92a, 92b comprises a plurality of ridges or teeth 94 extending toward the proximal edge of the pin 90 (FIG. 3B). The anchor pin 90 may be inserted prongs-first (e.g., distal edge) into the opening 87 of the expansion wedge 80 (FIG. 3B). In some aspects, the leading edge of each prong 92a, 92b contacts the spur 89, and the shape of the spur 89 directs each prong 92a, 92b outward and into each channel 86. For example, one prong 92a will extend into the top channel 86, and the other prong 92b will extend into the bottom channel 86.

When the expansion wedge 80 is fully inserted into the socket 70, each channel 86 preferably aligns with each slot 16, 26 on the main body of the implant 1. Thus, when the anchor pin 90 is inserted into the expansion wedge 80, each prong 92a, 92b passes through each channel 86, and extends into and ultimately out from each slot 16, 26 (FIGS. 4A-4D). The ridges or teeth 94 preferably engage a notch, catch or pawl 17 (top portion 10), 27 (bottom portion 20) on each slot 16, 26, effectively locking the anchor pin 90 in place, and preventing expulsion of the anchor pin 90 from each slot 16, 26 and each channel 86.

When the anchor pin 90 is fully engaged with the implant 1 (including the expansion wedge 80), the distal edges of each prong 92a, 92b extend out from top surface 12 and bottom surface 22 of the implant 1. Each distal edge preferably engages vertebral endplate bone, and helps resist expulsion of the implant 1 from the intervertebral space, and preferably also facilitates integration of the implant 1. The distal edges of each prong 92a, 92b may comprise a roughened surface topography 18, including a roughened surface topography 18 as described or exemplified herein, and including macro features, micro features, and nano features.

Roughened surface topography on the prongs 92a, 92b may enhance integration of the implant 1 with the vertebral end plate bone.

The anchor pin 90 may be fabricated from any suitable material. The anchor pin 90 is preferably sufficiently rigid to engage vertebral endplate bone and not break under load stress once the implant 1 is implanted, yet the pin 90 is also sufficiently flexible to extend as directed through each channel 86 and slot 16, 26.

In some aspects, the implant 1 comprises at least one vertical aperture 60 that extends the entire height H of the implant 1. The vertical aperture 60 has a size and shape for maximizing the surface area of the top surface 12 and the bottom surface 22 available for contacting vertebral endplate bone and maximizing the contact of a bone graft material with vertebral endplate bone, when a bone graft material is disposed in the aperture 60 such that it may make contact with the vertebral endplate bone. The vertical aperture 60 may further define a transverse rim 62 having a greater posterior portion width P than an anterior portion width A, or an equal posterior portion width P and anterior portion width A. The posterior portion width P may comprise the distance between the posterior edge of the implant 1 and the posterior edge of the vertical aperture 60. The transverse rim 62 effectively surrounds the vertical aperture 60. The vertical aperture 60 may extend through the implant 1, from the top surface 12 through the bottom surface 22, and may contain a bone graft material as described herein.

The posterior portion width P may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The anterior portion width A may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. In some aspects, the transverse rim 62 has a generally large surface area and contacts the vertebral endplate. The transverse rim 62 may act to better distribute contact stresses upon the implant 1, and hence minimize the risk of subsidence while maximizing contact with the apophyseal supportive bone.

The posterior portion width P and/or anterior portion width A comprise dimensions of the implant top surface 12 or bottom surface 22. Measured from the edge of one lateral side 30 to the edge of the other lateral side 30, the top surface 12 and bottom surface 22 may be about 5 mm to about 50 mm in width, and in some aspects may be about 7 mm to about 15 mm, about 8 mm to about 12 mm, about 9 mm to about 12 mm, about 9 mm to about 11 mm, about 10 mm to about 20 mm, about 10 mm to about 18 mm, about 10 mm to about 17 mm, about 11 mm to about 19 mm, about 11 mm to about 17 mm, about 12 mm to about 17 mm, about 12 mm to about 16 mm, about 15 mm to about 25 mm, about 15 mm to about 23 mm, about 16 mm to about 24 mm, about 16 mm to about 23 mm, about 17 mm to about 24 mm, about 17 mm to about 23 mm, about 18 mm to about 22 mm, about 20 mm to about 25 mm, about 20 mm to about 22 mm, about 30 mm to about 50 mm, about 30 mm to about 48 mm, about 30 mm to about 45 mm, about 30 mm to about 42 mm, about 31 mm to about 45 mm, about 31 mm to about 43 mm, about 31 mm to about 41 mm, about 32 mm to about 42 mm, or about 32 mm to about 40 mm in width. Measured from the edge of one lateral side 30 to the edge of the other lateral side 30, the top surface 12 and bottom surface 22 may be about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 25 mm, about 30 mm, about 31 mm, about 32 mm, about 33 mm, about 34 mm, about 35 mm, about 36 mm, about 37 mm, about 38 mm, about 39 mm, or about 40 mm in width.

Measured from the edge of the posterior portion 50, to the edge of the anterior portion 40, the top surface 12 and bottom surface 22 may be about 10 mm to about 70 mm in length, and in some aspects may be about 10 mm to about 20 mm, about 10 mm to about 18 mm, about 11 mm to about 19 mm, about 11 mm to about 18 mm, about 11 mm to about 17 mm, about 12 mm to about 16 mm, about 18 mm to about 34 mm, about 18 mm to about 32 mm, about 20 mm to about 34 mm, about 20 mm to about 32 mm, about 20 mm to about 31 mm, about 20 mm to about 30 mm, about 20 mm to about 28 mm, about 20 mm to about 27 mm, about 21 mm to about 32 mm, about 21 mm to about 30 mm, about 21 mm to about 28 mm, about 21 mm to about 27 mm, about 22 mm to about 32 mm, about 22 mm to about 31 mm, about 30 mm to about 70 mm, about 35 mm to about 65 mm, about 38 mm to about 64 mm, about 38 mm to about 62 mm, about 38 mm to about 60 mm, about 39 mm to about 62 mm, about 39 mm to about 61 mm, or about 40 mm to about 60 mm in length. Measured from the edge of the posterior portion 50 to the edge of the anterior portion 40, the top surface 12 and bottom surface 22 may be about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 35 mm, about 40 mm, about 45 mm, about 55 mm, or about 60 mm in length.

The size and shape of the vertical aperture 60 is carefully chosen to achieve a preferable design tradeoff for the particular application envisioned for the implant 1. The vertical aperture 60 preferably maximizes the surface area of the top surface 12 and/or bottom surface 22, while at the same time maximizing both the capacity for radiographic visualization and access to the bone graft material. It is highly preferred that the bone graft material bear at least some of the load forces of the spine once the implant 1 is implanted.

The vertical aperture 60 comprises a maximum width at its center, the size of this width ranges from about 40% to about 80% of the distance (e.g., width) between the edges of the opposing lateral sides. The width may range from about 40% to about 60%, about 45% to about 75%, about 50% to about 70%, about 50% to about 80%, about 55% to about 65%, about 55% to about 70%, about 55% to about 75%, about 60% to about 75%, or about 60% to about 80% of the distance between the edges of the opposing lateral sides The vertical aperture 60 may be in communication with the slot 16 on the top portion and with the slot 26 on the bottom portion 26, as shown in FIG. 5A, FIG. 5B, and FIG. 5C. In some aspects, the vertical aperture 60 preferably aligns with a vertical aperture 96 that extends through the expansion wedge 80 (FIG. 6A). Thus, when the expansion wedge 80 is fully inserted into the implant socket 70, a void extends through the top surface 12, the vertical aperture 60 on the implant 1 body, the vertical aperture 96 on the expansion wedge 80, and the bottom surface 22 (FIG. 6B). The bone graft material may thus be contained by the expansion wedge vertical aperture 96. The expansion wedge vertical aperture 96 preferably is not in communication with the opening 87 or the channels 86.

When the expansion wedge 80 is fully inserted into the socket 70 of an implant 1 comprising a vertical aperture 60, the expansion wedge vertical aperture 96 preferably aligns with the implant vertical aperture 60, and each channel 86 preferably aligns with each slot 16, 26 on the main body of the implant 1 (FIG. 6B, FIG. 6C, and FIG. 7A). Thus, when the anchor pin 90 is inserted into the expansion wedge 80 (FIGS. 7B-7D), each prong 92a, 92b passes through each channel 86, and extends into and ultimately out from each slot 16, 26 (FIGS. 7B-7D). Each prong 92a, 92b may project above the vertical aperture 60. In embodiments comprising a vertical aperture 60 on the implant 1, the ridges or teeth 94 preferably engage a notch, catch, or pawl 17 (top portion 10), 27 (bottom portion 20) on each slot 16, 26, effectively locking the anchor pin 90 in place, and preventing expulsion of the anchor pin 90 from each slot 16, 26 and each channel 86.

FIG. 1A-FIG. 7D show examples of embodiments of the interbody spinal implant 1 suitable for use in an ALIF procedure. Other embodiments of the implant are better suited for PLIF, TLIF, or cervical fusion procedures. Thus, the invention also features embodiments an interbody spinal implant 101 especially well adapted for use in a PLIF procedure. The implant 101 may comprise a substantially rectangular shape, or in a variation, may comprise a curved shape. An implant comprising a curved shape is designated as implant 101a; because the features of the implant 101a illustrated in the drawings are the same as those of the implant 101, these features are given the same reference numbers, with the addition of the letter "a," (e.g., 101 and 101a) and are not described further. The curved implant 101a is suitable for a PLIF or TLIF procedure.

In preferred embodiments, the interbody spinal implant 101, 101a is comprised of two primary sections, a top portion 110, 110a, and a bottom portion 120, 120a. The top portion 110, 110a comprises a top surface 112, 112a and the bottom portion 120, 120a comprises a bottom surface 122, 122a. The top portion 110, 110a and bottom portion 120, 120a preferably are not directly connected to each other such that they may be separated when the implant 101, 101a expands, as detailed below. The top portion 110, 110a and bottom portion 120, 120a may be indirectly connected to each other through at least one movable joint (not shown) that holds these portions together to form the implant 101, 101a. When the implant 101, 101a is not expanded, the at least one movable joint is/are substantially closed such that the top portion 110, 110a and bottom portion 120, 120a may nevertheless contact each other, or at least be proximal to each other, as shown in FIGS. 8A-8D. When the implant expands, the at least one movable joint opens such that the top portion 110, 110a and bottom portion 120, 120a separate, but do not become detached from the implant 101, 101a. The movable joint is operably connected to each of the top portion 110, 110a and bottom portion 120, 120a. One or more of the top surface 112, 112a and the bottom surface 122, 122a comprises a roughened surface topography 118, 118a.

The top portion 110, 110a comprises an anterior side 114, 114a, a posterior side 115, 115a and opposing lateral sides 113, 113a. The bottom portion 120, 120a comprises an anterior side 124, 124a, a posterior side 125, 125a, and opposing lateral sides 123, 123a. The anterior sides 114, 114a and 124, 124a together comprise an anterior face 140, 140a of the implant 101, 101a. The posterior sides 115, 115a and 125, 125a together comprise a posterior face 150, 150a of the implant 101, 101a. The opposing lateral sides 113, 113a and 123, 123a together comprise opposing lateral faces 130, 130a of the implant 101, 101a. In some aspects, the interbody spinal implant 101 has a generally rectangular-shaped transverse cross-section, with smooth, blunted, or rounded opposing lateral faces 130 and anterior-lateral corners. In some aspects, the interbody spinal implant 101a has a generally parabolic- or curved-shaped transverse cross-section, with smooth, blunted, or rounded opposing lateral faces 130a and anterior-lateral corners. The anterior portion 140, 140a may be tapered to facilitate insertion of the implant 101, 101a. To further facilitate insertion, the implant 101, 101a may comprise chamfers at the corners of each posterior side 115, 115a (not shown). The chamfers may prevent the implant 101, 101a from catching upon insertion.

In preferred aspects, the implant 101, 101a comprises a socket 170, 170a with an opening 174, 174a to the socket 170, 170a on the posterior face 150, 150a (FIG. 8A and FIG. 8D). The socket 170, 170a receives an expansion wedge 180, 180a (FIG. 8A and FIG. 8E). The opening 174, 174a is comprised of a section of each of the posterior sides 115, 115a and 125, 125a. In some aspects, the socket 170, 170a is configured or includes engagement structures 172, 172a to facilitate insertion and placement of the implant 101, 101a by the practitioner during an implant procedure. For example, such configurations or engagement structures 172, 172a may receive and engage a surgical tool, and the surgical tool may be used to move the implant 1 about the intervertebral space. The structures 172, 172a may comprise screw threads 172, 172a, ribs 172, 172a, one or more notches 172, 172a, one or more lips 172, 172a, ridges 172, 172a, flanges 172, 172a, barbs 172, 172a, grooves 172, 172a or any combination thereof, to enhance engagement with a surgical tool to reduce the possibility of the surgical tool slipping out of the engagement structures 172, 172a. The top portion 110, 110a and the bottom portion 120, 120a of the implant 101, 101a each preferably comprise a slot 116, 116a (top portion 110, 110a), 126, 126a (bottom portion 120, 120a) near the posterior side 115, 115a or 125, 125a and extending from the top surface 112, 112a and through the top portion 110, 110a, and extending from the bottom surface 122, 122a and through the bottom portion 120, 120a, and into the socket 170 170a (FIGS. 8A-8D).

The expansion wedge 180, 180a is inserted into the opening 174, 174a and advanced into the socket 170, 170a (FIG. 9A-FIG. 9C). The expansion wedge 180, 180a comprises a top surface 181, 181a, a bottom surface 182, 182a, opposing lateral sides 183, 183a, an anterior face 184, 184a, and a posterior face 185. 185a Generally, the anterior face 184, 184a is the section that is first inserted into the opening 174, 174a.

The expansion wedge 180, 180a comprises at least one channel 186, 186a on each of the top 181, 181a and bottom surfaces 182, 182a. The expansion wedge 180, 180a also comprises at least one opening 187, 187a on the posterior face 185, 185a (FIG. 8A-FIG. 8D, and FIG. 9B and FIG. 9C). The opening 187, 187a is preferably in communication with each channel 186, 186a. The opening 187, 187a preferably receives the prongs 192, 192a of an anchor pin 190, 190a (FIG. 9B and FIG. 9C). The opening 187, 187a may comprise one or more engagement structures 188, 188a to facilitate insertion and placement of the expansion wedge 180, 180a into the socket 170, 170a of the implant 101, 101a, and/or insertion and placement of the implant 101, 101a by the practitioner during an implant procedure. The engagement structures 188, 188a may comprise screw threads 188, 188a, ribs 188, 188a, one or more notches 188, 188a, one or more lips 188, 188a, ridges 188, 188a, flanges 188, 188a, barbs 188, 188a, grooves 188, 188a or any combination thereof. The engagement structures 188, 188*a* may receive and engage a surgical tool, and the surgical tool may be used to move the implant 101, 101*a* about the intervertebral space. For example, once the expansion wedge 180, 180*a* is fully inserted into the socket 170, 170*a*, the structures 172, 172*a* on the socket 170, 170*a* may no longer be fully accessible such that the structures 188, 188*a* of the wedge 180, 180*a* stand in the place of the structures 172, 172*a* of the socket to allow further manipulation of the implant 101, 101*a* by surgical tools within the intervertebral space. The expansion wedge 180, 180*a* may also comprise a wedge-shaped spur 189, 189*a* (FIG. 9B and FIG. 9C) that may separate and force the prongs 192, 192*a* of the anchor pin 190, 190*a* outward and through each channel 186, 186*a*.

The expansion wedge 180, 180*a* may also comprise a spur 189, 189*a* that may separate and force the prongs 192, 192*a* of the anchor pin 190, 190*a* outward and through each channel 186, 186*a*. The spur 189, 189*a* is preferably substantially wedge-shaped. As the prongs 192, 192*a* of the anchor pin 190, 190*a* are advanced into the wedge 180, 180*a* they contact the spur 189, 189*a* and are separated and directed toward and into each channel 186, 186*a*.

The anterior face 184, 184*a* of the expansion wedge 180, 180*a* comprises a first height h, and the posterior face 185, 185*a* of the expansion wedge 180, 180*a* comprises a second height h' that is preferably greater than the first height h. The first height h allows the anterior face 184, 184*a* to fit within the opening 174, 174*a* of the implant 101, 101*a*.

The first height h may be about 0.5 mm to about 20 mm, about 1 mm to about 3 mm, about 1 mm to about 5 mm, about 1 mm to about 7 mm, about 1 mm to about 10 mm, about 1 mm to about 12 mm, about 1 mm to about 15 mm, about 1 mm to about 18 mm, about 2 mm to about 4 mm, about 2 mm to about 5 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 20 mm, about 3 mm to about 5 mm, about 3 mm to about 7 mm, about 3 mm to about 10 mm, about 3 mm to about 14 mm, about 3 mm to about 16 mm, about 4 mm to about 6 mm, about 4 mm to about 8 mm, about 4 mm to about 12 mm, about 5 mm to about 10 mm, about 5 mm to about 15 mm, about 5 mm to about 20 mm, about 6 mm to about 8 mm, about 6 mm to about 10 mm, about 8 mm to about 12 mm, about 8 mm to about 15 mm, about 8 mm to about 18 mm, about 10 mm to about 15 mm, about 10 mm to about 20 mm, or about 15 mm to about 18 mm. The second height h' may be about 0.5 mm to about 15 mm, about 1 mm to about 3 mm, about 1 mm to about 5 mm, about 1 mm to about 7 mm, about 1 mm to about 10 mm, about 1 mm to about 12 mm, about 1 mm to about 15 mm, about 2 mm to about 4 mm, about 2 mm to about 5 mm, about 2 mm to about 6 mm, about 2 mm to about 8 mm, about 2 mm to about 10 mm, about 2 mm to about 12 mm, about 3 mm to about 5 mm, about 3 mm to about 7 mm, about 3 mm to about 10 mm, about 4 mm to about 6 mm, about 4 mm to about 8 mm, about 4 mm to about 12 mm, about 5 mm to about 10 mm, about 6 mm to about 8 mm, or about 6 mm to about 10 mm. The first height h and second height h' may independently be about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm, about 13 mm, about 14 mm, about 15 mm, about 16 mm, about 17 mm, about 18 mm, about 19 mm, or about 20 mm.

The socket 170, 170*a* preferably comprises a wedge shape that accommodates the shape of the expansion wedge 180, 180*a*. In this manner, the internal surfaces of the socket 170, 170*a* contact the top surface 181, 181*a* and bottom surface 182, 182*a* of the expansion wedge 180, 180*a* (e.g., FIG. 9B and FIG. 9C). Thus, for example, when the expansion wedge 180, 180*a* is fully inserted into the socket 170, 170*a*, the posterior face 185, 185*a*, which has a smaller height (h') than the anterior face 184, 184*a* maintains contact with a socket surface 170, 170*a* and does not "float" freely within the center of the implant 101, 101*a*. This helps to ensure that the load is distributed on all surfaces of the expansion wedge 180, 180*a* without the load being exerted primarily on the highest point of the anterior face 184, 184*a*.

As the expansion wedge 180, 180*a* is inserted into the socket 170, 170*a*, the implant 101, 101*a* expands, thereby increasing in height H. As the expansion wedge 180, 180*a* advances inward, it forces each of the top portion 110, 110*a* and bottom portion 120, 120*a* of the implant 101, 101*a* apart, thereby increasing the distance between them and increasing the height H. Preferably, the height H increases proportionally with the second height h' of the expansion wedge 180, 180*a*. The implant 101, 101*a* is preferably compatible with expansion wedges 180, 180*a* having different first heights h and/or second heights h', thereby allowing the implant 101, 101*a* to be expanded to a desired height H, for example, to accommodate different intervertebral space heights or other conditions of the subject into which the implant 101, 101*a* is implanted.

Optionally, the expansion wedge 180, 180*a* may comprise one or more structures to resist expulsion of the wedge 180, 180*a* from the socket 170, 170*a*, once fully inserted. The structures may comprise a ratchet or tabs (not shown). The expansion wedge 180, 180*a* may be freely inserted and removed from the socket, and in some aspects does not include any structures to resist expulsion from the socket 170, 170*a*.

The wedge 180, 180*a* may be fabricated from any suitable materials. The wedge 180, 180*a* is preferably sufficiently rigid to hold the top 110, 110*a* and bottom 120, 120*a* portions of the implant 101, 101*a* apart and not break under load stress once the implant 101, 101*a* is implanted. The wedge 180, 180*a* may be fabricated from a metal, a plastic, or a composite, and the material is preferably biocompatible.

The anchor pin 190, 190*a* comprises at least two flexible prongs 192*a*, 192*b*, 192*a*-*a*, 192*a*-*b* preferably spaced apart. Each prong 192*a*, 192*b*, 192*a*-*a*, 192*a*-*b* comprises a plurality of ridges or teeth 194, 194*a* extending toward the exterior of the pin 190, 190*a* (FIG. 9A-FIG. 10C). The anchor pin 190, 190*a* may be inserted prongs-first (e.g., distal edge) into the opening 187, 187*a* of the expansion wedge 180, 180*a* (FIG. 9B-FIG. 10A). In some aspects, the leading edge of each prong 192*a*, 192*b*, 192*a*-*a*, 192*a*-*b* contacts the spur 189, 189*a*, and the shape of the spur 189, 189*a* directs each prong 192*a*, 192*b*, 192*a*-*a*, 192*a*-*b* outward and into each channel 186, 186*a* (FIG. 9B and FIG. 9C). For example, one prong 192*a*, 192*a*-*a* will extend into the top channel 186, 186*a*, and the other prong 192*b*, 192*a*-*b* will extend into the bottom channel 186, 186*a*.

When the expansion wedge 180, 180*a* is fully inserted into the socket 170, 170*a*, each channel 186, 186*a* preferably aligns with each slot 116, 116*a*, 126, 126*a* on the main body of the implant 101, 101*a*. Thus, when the anchor pin 190, 190*a* is inserted into the expansion wedge 180, 180*a*, each prong 192*a*, 192*b*, 192*a*-*a*, 192*a*-*b* passes through each channel 186, 186*a*, and extends into and ultimately out from each slot 116, 116*a*, 126, 126*a* (FIG. 9A, FIG. 10B, FIG.

10C). The ridges or teeth 194, 194a preferably engage a catch or pawl 117, 117a (top portion 110, 110a), 127, 127a (bottom portion 120, 120a) on each slot 116, 116a, 126, 126a effectively locking the anchor pin 190, 190a in place, and preventing expulsion of the anchor pin 190, 190a from each slot 116, 116a, 126, 126a and each channel 186, 186a.

When the anchor pin 190, 190a is fully engaged with the implant 101, 101a (including the expansion wedge 180, 180a), the distal edges of each prong 192a, 192b, 192a-a, 192a-b extend out from top surface 112, 112a and bottom surface 122, 122a of the implant 101, 101a. Each distal edge preferably engages vertebral endplate bone, and helps resist expulsion of the implant 101, 101a from the intervertebral space, and preferably also facilitates integration of the implant 101, 101a. The distal edges of each prong 192a, 192b, 192a-a, 192a-b may comprise a roughened surface topography 118, 118a, including a roughened surface topography 118, 118a as described or exemplified herein, and including macro features, micro features, and nano features. Roughened surface topography on the prongs 192a, 192b, 192a-a, 192a-b may enhance integration of the implant 1 with the vertebral end plate bone.

The anchor pin 190, 190a may be fabricated from any suitable material. The anchor pin 190, 190a is preferably sufficiently rigid to engage vertebral endplate bone and not break under load stress once the implant 101, 101a is implanted, yet the pin 190, 190a is also sufficiently flexible to extend as directed through each channel 186, 186a and slot 116, 116a, 126, 126a. The anchor pin 190, 190a may be fabricated from a metal, a plastic, or a composite, and the material is preferably biocompatible.

In some aspects, the implant 101, 101a comprises at least one vertical aperture 160, 160a that extends the entire height H of the implant 101, 101a. The vertical aperture 160, 160a has a size and shape for maximizing the surface area of the top surface 112, 112a and the bottom surface 122, 122a available for contacting vertebral endplate bone and maximizing the contact of a bone graft material with vertebral endplate bone, when a bone graft material is disposed in the aperture 160, 160a such that it may make contact with the vertebral endplate bone. The vertical aperture 160, 160a may further define a transverse rim 162, 162a having a greater posterior portion width P than an anterior portion width A, or an equal posterior portion width P and anterior portion width A. The posterior portion width P may comprise the distance between the posterior edge of the implant 101, 101a and the posterior edge of the vertical aperture 160, 160a. The transverse rim 162, 162a effectively surrounds the vertical aperture 160, 160a. The vertical aperture 160, 160a may extend through the implant 101, 101a, from the top surface 112, 112a through the bottom surface 122, 122a, and may contain a bone graft material as described herein.

The posterior portion width P may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The anterior portion width A may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. In some aspects, the transverse rim 162, 162a has a generally large surface area and contacts the vertebral endplate. The transverse rim 162, 162a may act to better distribute contact stresses upon the implant 101, 101a, and hence minimize the risk of subsidence while maximizing contact with the apophyseal supportive bone.

The posterior portion width P may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The anterior portion width A may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. In some aspects, the transverse rim 162, 162a has a generally large surface area and contacts the vertebral endplate. The transverse rim 162, 162a may act to better distribute contact stresses upon the implant 101, 101a, and hence minimize the risk of subsidence while maximizing contact with the apophyseal supportive bone.

The posterior portion width P and/or anterior portion width A comprise dimensions of the implant top surface 112, 112a or bottom surface 122, 122a. Measured from the edge of one lateral side 130, 130a to the edge of the other lateral side 130, 130a, the top surface 112, 112a and bottom surface 122, 122a may be about 5 mm to about 50 mm in width, and in some aspects may be about 7 mm to about 15 mm, about 8 mm to about 12 mm, about 9 mm to about 12 mm, about 9 mm to about 11 mm, about 10 mm to about 20 mm, about 10 mm to about 18 mm, about 10 mm to about 17 mm, about 11 mm to about 19 mm, about 11 mm to about 17 mm, about 12 mm to about 17 mm, about 12 mm to about 16 mm, about 15 mm to about 25 mm, about 15 mm to about 23 mm, about 16 mm to about 24 mm, about 16 mm to about 23 mm, about 17 mm to about 24 mm, about 17 mm to about 23 mm, about 18 mm to about 22 mm, about 20 mm to about 25 mm, about 20 mm to about 22 mm, about 30 mm to about 50 mm, about 30 mm to about 48 mm, about 30 mm to about 45 mm, about 30 mm to about 42 mm, about 31 mm to about 45 mm, about 31 mm to about 43 mm, about 31 mm to about 41 mm, about 32 mm to about 42 mm, or about 32 mm to about 40 mm in width. Measured from the edge of one lateral side 130, 130a to the edge of the other lateral side 130, 130a, the top surface 112, 112a and bottom surface 122, 122a may be about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 25 mm, about 30 mm, about 31 mm, about 32 mm, about 33 mm, about 34 mm, about 35 mm, about 36 mm, about 37 mm, about 38 mm, about 39 mm, or about 40 mm in width.

Measured from the edge of the posterior portion 150, 150a, to the edge of the anterior portion 140, 140a, the top surface 112, 112a and bottom surface 122, 122a may be about 10 mm to about 70 mm in length, and in some aspects may be about 10 mm to about 20 mm, about 10 mm to about 18 mm, about 11 mm to about 19 mm, about 11 mm to about 18 mm, about 11 mm to about 17 mm, about 12 mm to about 16 mm, about 18 mm to about 34 mm, about 18 mm to about 32 mm, about 20 mm to about 34 mm, about 20 mm to about 32 mm, about 20 mm to about 31 mm, about 20 mm to about 30 mm, about 20 mm to about 28 mm, about 20 mm to about 27 mm, about 21 mm to about 32 mm, about 21 mm to about 30 mm, about 21 mm to about 28 mm, about 21 mm to about 27 mm, about 22 mm to about 32 mm, about 22 mm to about 31 mm, about 30 mm to about 70 mm, about 35 mm to about 65 mm, about 38 mm to about 64 mm, about 38 mm to about 62 mm, about 38 mm to about 60 mm, about 39 mm to about 62 mm, about 39 mm to about 61 mm, or about 40 mm to about 60 mm in length. Measured from the edge of the posterior portion 150, 150a to the edge of the anterior portion 140, 140a, the top surface 112, 112a and bottom surface 122, 122a may be about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 35 mm, about 40 mm, about 45 mm, about 55 mm, or about 60 mm in length.

The size and shape of the vertical aperture 160, 160a is carefully chosen to achieve a preferable design tradeoff for the particular application envisioned for the implant 101, 101a. The vertical aperture 160, 160a preferably maximizes the surface area of the top surface 112, 112a and/or bottom surface 122, 122a while at the same time maximizing both the capacity for radiographic visualization and access to the bone graft material. It is highly preferred that the bone graft material bear at least some of the load forces of the spine once the implant 101, 101a is implanted.

The vertical aperture 160, 160a comprises a maximum width at its center, the size of this width ranges from about 40% to about 80% of the distance (e.g., width) between the edges of the opposing lateral sides. The width may range from about 40% to about 60%, about 45% to about 75%, about 50% to about 70%, about 50% to about 80%, about 55% to about 65%, about 55% to about 70%, about 55% to about 75%, about 60% to about 75%, or about 60% to about 80% of the distance between the edges of the opposing lateral sides.

Figure 11A:
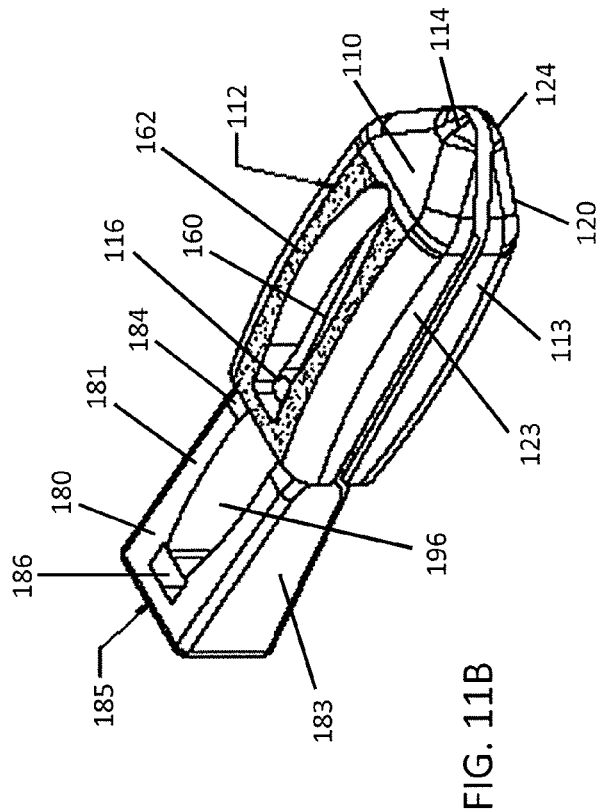
FIG. 11A shows a posterior perspective of an embodiment of a PLIF expandable implant having a vertical aperture extending from the top portion through the bottom portion, with an expansion wedge having a vertical aperture extending from its top surface through its bottom surface and aligned for insertion into the implant.
Figure 11B:
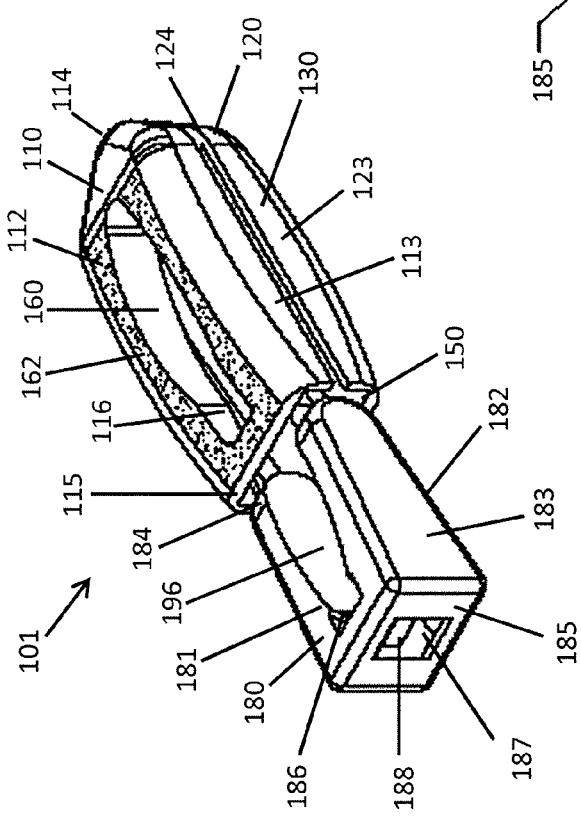
FIG. 11B shows an anterior perspective of an embodiment of a PLIF expandable implant having a vertical aperture extending from the top portion through the bottom portion, with an expansion wedge having a vertical aperture extending from its top surface through its bottom surface and aligned for insertion into the implant.
Figure 11C:
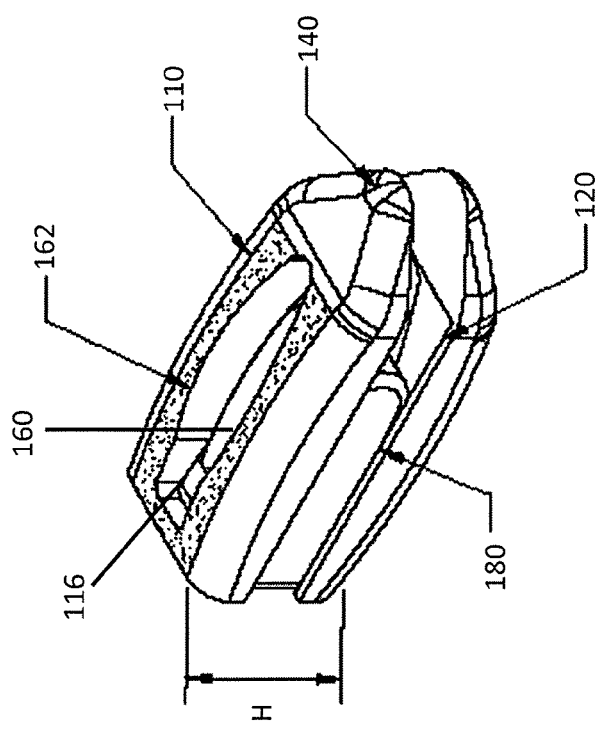
FIG. 11C shows a perspective of an embodiment of a PLIF expandable implant having a vertical aperture, with the expansion wedge having a vertical aperture inserted into the implant.
Figure 11D:
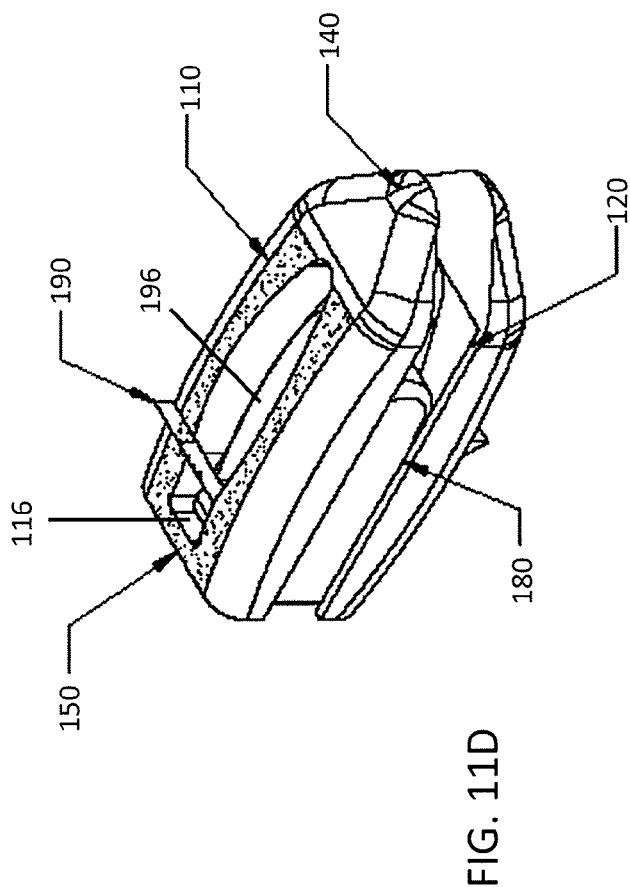
FIG. 11D shows a perspective of an embodiment of a PLIF expandable implant having a vertical aperture, with the expansion wedge having a vertical aperture inserted into the implant, with an anchor pin secured in place.
Figures 12A, 12B:
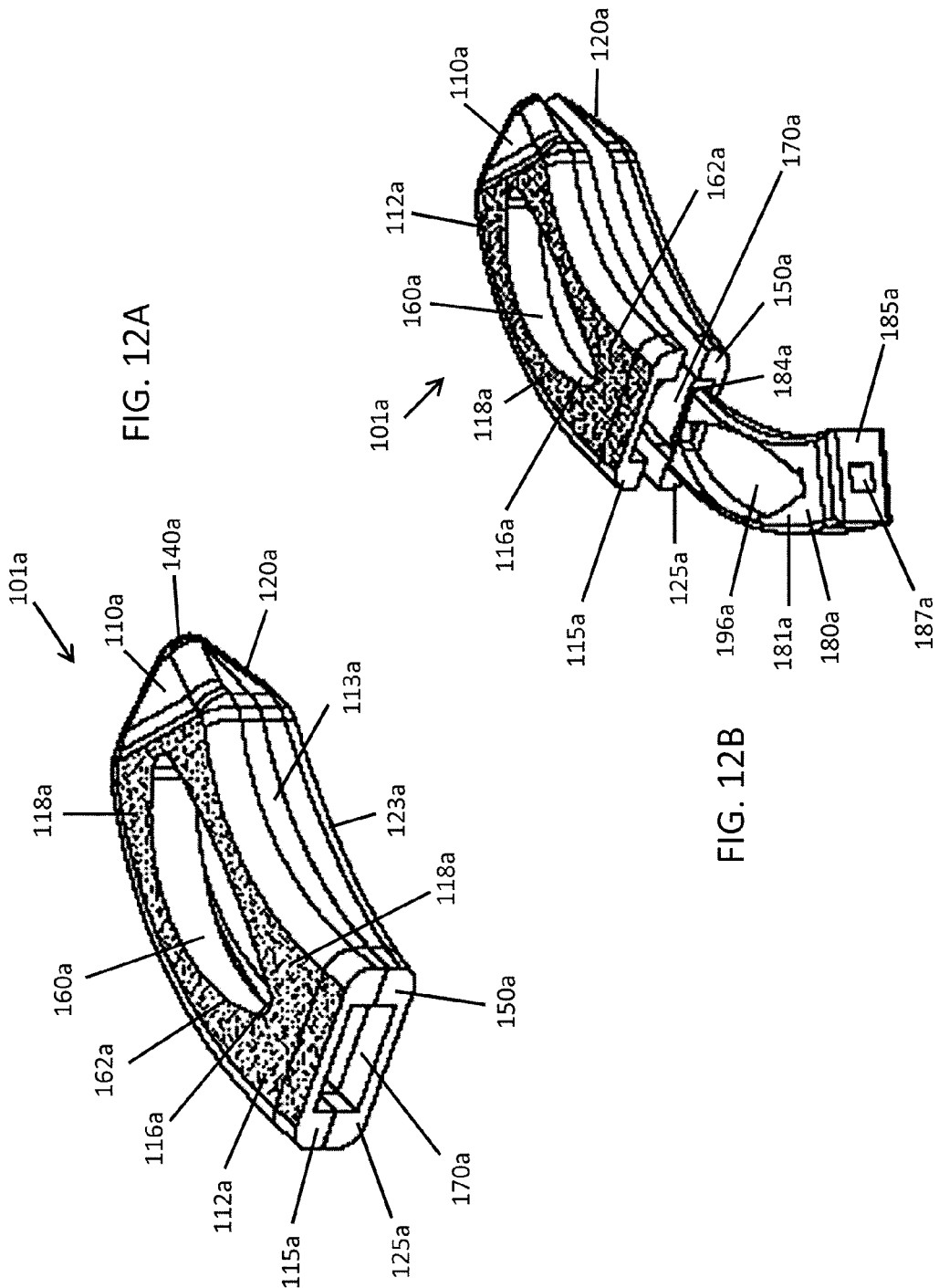
FIG. 12A shows a posterior perspective of an embodiment of a curved PLIF expandable implant having a vertical aperture extending from the top portion through the bottom portion.
FIG. 12B shows a posterior perspective of an embodiment of a curved PLIF expandable implant having a vertical aperture extending from the top portion through the bottom portion, with an expansion wedge having a vertical aperture extending from its top surface through its bottom surface and aligned for insertion into the implant.

The vertical aperture 160, 160a may be in communication with the slot 116, 116a on the top portion and with the slot 126, 126a on the bottom portion 126, 126a, as shown in FIGS. 11A-12D. In some aspects, the vertical aperture 160, 160a preferably aligns with a vertical aperture 196, 196a that extends through the expansion wedge 180, 180a (FIG. 11A, FIG. 11B, FIG. 12B). Thus, when the expansion wedge 180, 180a is fully inserted into the implant socket 170, 170a, a void extends through the top surface 112, 112a, the vertical aperture 160, 160a on the implant 101, 101a body, the vertical aperture 196, 196a on the expansion wedge 180, 180a and the bottom surface 122, 122a (FIG. 11B, FIG. 12C). The bone graft material may thus be contained by the expansion wedge vertical aperture 196, 196a. The expansion wedge vertical aperture 196, 196a preferably is not in communication with the opening 187, 187a or the channels 186, 186a.

When the expansion wedge 180, 180a is fully inserted into the socket 170, 170a of an implant 101, 101a comprising a vertical aperture 160, 160a, the expansion wedge vertical aperture 196, 196a preferably aligns with the implant vertical aperture 160, 160a, and each channel 186, 186a preferably aligns with each slot 116, 116a, 126, 126a on the main body of the implant 101, 101a. Thus, when the anchor pin 190, 190a is inserted into the expansion wedge 180, 180a (FIG. 11D and FIG. 12D), each prong 192a, 192b, 192a-a, 192a-b passes through each channel 186, 186a, and extends into and ultimately out from each slot 116, 116a, 126, 126a. Each prong 192a, 192b, 192a-a, 192a-b may project above the vertical aperture 160, 160a. In embodiments comprising a vertical aperture 160, 160a on the implant 101, 101a the ridges or teeth 194, 194a preferably engage a catch or pawl 117, 117a (top portion 110, 110a), 127, 127a (bottom portion 120, 120a) on each slot 116, 116a, 126, 126a effectively locking the anchor pin 190, 190a in place, and preventing expulsion of the anchor pin 190, 190a from each slot 116, 116a, 126, 126a and each channel 186, 186a.

It is believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration. The roughened topography 18, 118, 118a may better promote the ultimate osteointegration of the implant 1, 101, 101a, and complements the anti-expulsion and anti-migration activity of the anchor pin 90, 190, 190a by gripping the vertebral endplate surfaces. In some embodiments, the implant 1, 101, 101a does not include the roughened topography 18, 118, 118a.

The roughened surface topography 18, 118, 118a may be comprised of macro-scale features, micro-scale features, and nano-scale features. For example, the roughened surface topography 18, 118, 118a may be obtained by combining separate macro processing, micro processing, and nano processing steps. Macro features include relatively large dimensions, for example, dimensions measured in millimeters (mm) or microns (μm). Micro features include dimensions that are measured in microns (μm). Nano features include dimensions that are measured in nanometers (nm).

The shapes of the frictional surface protrusions of the roughened surface topography 18, 118, 118a may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. In practice, "Ra" is the most commonly used roughness parameter. It is the arithmetic average height. Mathematically, Ra is computed as the average distance between each roughness profile point and the mean line. In mathematical terms, this process can be represented as Equation 1:

$$Ra = \frac{1}{n}\sum_{i=1}^{n} |y_i|$$

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value.

The maximum peak-to-valley height, Rmax, is the maximum peak-to-valley distance in a single sampling length. The mean spacing, Sm, is the average spacing between positive mean line crossings. The distance between each positive (upward) mean line crossing is determined and the average value is calculated. The parameters Sm, Rmax, and Ra can be used define the surface roughness following formation of each of the three types of features macro, micro, and nano.

The macro features for each of the three parameters may comprise the following preferred ranges (all measurements in microns). In some aspects, the macro mean spacing, Sm, is about 400 to about 2000 micrometers. More preferably, the macro mean spacing is about 750 to about 1750 micrometers, and more preferably, the macro mean spacing is about 1000 to about 1500 micrometers. In some aspects, the macro mean spacing is about 500 to about 1000 micrometers, about 600 to about 900 micrometers, about 700 to about 1000 micrometers, about 750 to about 1200 micrometers, about 800 to about 1300 micrometers, about 900 to about 1300 micrometers, about 1000 to about 1300 micrometers, about 1100 to about 1300 micrometers, about 1100 to about 1400 micrometers, about 1150 to about 1250 micrometers, about 1150 to about 1350 micrometers, about 1200 to about 1500 micrometers, or about 1200 to about 1400 micrometers. In some aspects, the macro peak-to-valley height, Rmax, is about 40 to about 500 micrometers. More preferably, the macro peak-to-valley height is about 150 to about 400 micrometers, and more preferably, about 250 to about 300 micrometers. In some aspects, the macro mean peak-to valley height is about 100 to about 450 micrometers, about 200 to about 400 micrometers, about 200 to about 300 micrometers, about 260 to about 280 micrometers, about 250 to about 350 micrometers, about 260 to about 320 micrometers, or about 270 to about 300 micrometers. In some aspects, the macro average amplitude, Ra, is about 20 to about 200 micrometers. More preferably, the macro average amplitude is about 50 to about 150 micrometers, and more preferably about 100 to about 120 micrometers. In some aspects, the macro average amplitude is about 80 to about 180 micrometers, about 90 to about 160 micrometers, about 90 to about 140 micrometers, about 100 to about 150 micrometers, about 100 to about 130 micrometers, about 105 to about 125 micrometers, or about 105 to about 115 micrometers.

The micro features for each of the three parameters may comprise the following preferred ranges (all measurements in microns). In some aspects, the micro mean spacing, Sm, is about 20 to about 400 micrometers. More preferably, the micro mean spacing is about 100 to about 300 micrometers, and more preferably, the macro mean spacing is about 200 to about 220 micrometers. In some aspects, the micro mean spacing is about 50 to about 350 micrometers, about 75 to about 350 micrometers, about 75 to about 300 micrometers, about 100 to about 325 micrometers, about 100 to about 250 micrometers, about 120 to about 220 micrometers, about 150 to about 250 micrometers, about 180 to about 240 micrometers, about 190 to about 230 micrometers, or about 205 to about 215 micrometers. In some aspects, the micro peak-to-valley height, Rmax, is about 2 to about 40 micrometers. More preferably, the micro peak-to-valley height is about 5 to about 25 micrometers, and more preferably, about 6 to about 16 micrometers. In some aspects, the micro mean peak-to valley height is about 0.5 to about 50 micrometers, about 1 to about 45 micrometers, about 1 to about 40 micrometers, about 1 to about 30 micrometers, about 1 to about 20 micrometers, about 1 to about 15 micrometers, about 2 to about 50 micrometers, about 2 to about 30 micrometers, about 2 to about 25 micrometers, about 3 to about 40 micrometers, about 3 to about 30 micrometers, about 4 to about 40 micrometers, about 4 to about 30 micrometers, about 5 to about 40 micrometers, about 5 to about 30 micrometers, about 7 to about 20 micrometers, about 7 to about 15 micrometers, about 8 to about 14 micrometers, or about 9 to about 13 micrometers. In some aspects, the micro average amplitude, Ra, is about 1 to about 20 micrometers. More preferably, the micro average amplitude is about 1 to about 10 micrometers, and more preferably about 3 to about 7 micrometers. In some aspects, the micro average amplitude is about 0.5 to about 30 micrometers, about 0.5 to about 25 micrometers, about 1 to about 15 micrometers, about 1 to about 10 micrometers, about 1 to about 9 micrometers, about 1 to about 7 micrometers, about 2 to about 9 micrometers, or about 4 to about 7 micrometers.

The nano features for each of the three parameters may comprise the following preferred ranges (all measurements in microns). In some aspects, the nano mean spacing, Sm, is about 0.5 to about 20 micrometers. More preferably, the nano mean spacing is about 5 to about 15 micrometers, and more preferably, the macro mean spacing is about 8 to about 12 micrometers. In some aspects, the nano mean spacing is about 0.1 to about 30 micrometers, about 0.25 to about 25 micrometers, about 0.5 to about 15 micrometers, about 0.5 to about 13 micrometers, about 1 to about 250 micrometers, about 1 to about 20 micrometers, about 1 to about 150 micrometers, about 2 to about 18 micrometers, about 2 to about 12 micrometers, about 7 to about 14 micrometers, or about 9 to about 11.5 micrometers. In some aspects, the nano peak-to-valley height, Rmax, is about 0.2 to about 2 micrometers. More preferably, the nano peak-to-valley height is about 0.5 to about 1.5 micrometers, and more preferably, about 0.8 to about 1.4 micrometers. In some aspects, the nano mean peak-to valley height is about 0.05 to about 5 micrometers, about 0.1 to about 3 micrometers, about 0.1 to about 2 micrometers, about 0.1 to about 1.5 micrometers, about 0.1 to about 0.4 micrometers, about 0.2 to about 3 micrometers, about 0.2 to about 2.5 micrometers, about 0.2 to about 1.8 micrometers, about 0.6 to about 1.6 micrometers, about 0.7 to about 1.5 micrometers, or about 0.9 to about 1.3 micrometers. In some aspects, the nano average amplitude, Ra, is about 0.01 to about 1 micrometers. More preferably, the nano average amplitude is about 0.05 to about 0.75 micrometers, and more preferably about 0.3 to about 0.7 micrometers. In some aspects, the nano average amplitude is about 0.005 to about 2 micrometers, about 0.005 to about 1.5 micrometers, about 0.01 to about 0.75 micrometers, about 0.01 to about 1.1 micrometers, about 0.01 to about 0.9 micrometers, about 0.01 to about 0.07 micrometers, about 0.025 to about 0.75 micrometers, or about 0.04 to about 0.6 micrometers.

The roughened topography 18, 118, 118a may be obtained through a variety of techniques including, without limitation, chemical etching, shot peening, plasma etching, laser etching, or abrasive blasting (such as sand or grit blasting). In at least one embodiment, the interbody spinal implant 1, 101, 101a may be comprised of titanium, or a titanium alloy, having the surface roughened topography 18, 118, 118a. The surfaces of the implant 1, 101, 101a are preferably bioactive (e.g., facilitate integration of the implant 1, 101, 101a).

The roughened topography 18, 118, 118a may be obtained via the repetitive masking and chemical or electrochemical milling processes described in U.S. Pat. No. 5,258,098; U.S. Pat. No. 5,507,815; U.S. Pat. No. 5,922,029; and U.S. Pat. No. 6,193,762. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.5 mm. Interbody spinal implants 1, 101, 101a in accordance with some preferred embodiments may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

In another example, the roughened surface topography 18, 118, 118a may also be provided by coating the implant 1, 101, 101a or anchor pin prongs 92a, 92b, 192a, 192b, 192a-a, 192b-a with a roughened topography material. For example, in some aspects, a material such as metal filings, shavings, or fine metal particles or powder, or fine plastic or polymeric particles may be laid onto the top surface 12, 112, 112a, or bottom surface 22, 122, 122a of the implant 1, 101, 101a, or vertebral bone-contacting surfaces of anchor pin prongs 92a, 92b, 192a, 192b, 192a-a, 192b-a according to any suitable method. In some aspects, an adhesive may be used to affix the material to the implant 1, 101, 101a or anchor pin prongs 92a, 92b, 192a, 192b, 192a-a, 192b-a. Plastic or polymeric materials may be spray-coated, airlaid, or melt-blown onto the implant 1, 101, 101a or anchor pin prongs 92a, 92b, 192a, 192b, 192a-a, 192b-a. The materials may be adhered directly, for example, by at least partially melting the particles such that they fuse to the desired surface when they cool. Metal materials may be cold sprayed or thermal sprayed onto the implant 1, 101, 101a, or anchor pin prongs 92a, 92b, 192a, 192b, 192a-a, 192b-a according to any suitable technique.

The implant 1, 101, 101a may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1, 101, 101a generally does not require extensive supplemental or obstructive implant instrumentation to maintain the prepared disc space during implantation. Thus, the interbody spinal implant 1, 101, 101a and associated implantation methods allow for larger-sized implants as compared with other size-limited interbody spinal implants known in the art. This advantage allows for greater medial-lateral width and correspondingly greater contact with the apophyseal rim.

The implant 1, 101, 101a may comprise a lordotic angle L, e.g., may be wedge-shaped to facilitate sagittal alignment. For example, in some aspects, the anterior portion 40, 140, 140a may comprise a height that is larger than the height of the posterior portion 50, 150, 150a. In some aspects, one of the lateral sides 30, 130, 130a may comprise a height that is larger than the height of the opposing lateral side 30, 130, 130a.

The lordotic angle L of the implant 1, 101, 101a preferably closely approximates, or otherwise is substantially the same as, the angle of lordosis of the spine of the patient where the implant 1, 101, 101a will be implanted. In some aspects, the implant 1, 101, 101a comprises a lordotic angle L that is about 3% to about 5% greater than the angle of lordosis of the spine into which the implant 1, 101, 101a is inserted. The implant 1, 101, 101a may comprise a lordotic angle L about 3%, about 3.3%, about 3.5%, about 3.7%, about 4%, about 4.3%, about 4.5%, about 4.7%, or about 5% greater than the patient's angle of lordosis, though percentages greater than 5% or lesser 3% are possible.

In addition to the roughened topography 18, 118, 118a, and the anchor pin 90, 190, 190a, the implant 1, 101, 101a may also comprise one or more sharp or anti-expulsion edges 8, 108, 108a to help resist movement and expulsion of the implant 1, 101, 101a after implantation. The roughened topography 18, 118, 118a promotes integration with the vertebral end plates over time, and the anchor pin 90, 190, 190a engages the vertebral end plates. To enhance movement resistance and provide additional stability under spinal loads in the body, particularly during the early stages of integration, the one or more sharp or anti-expulsion edges 8, 108, 108a may "dig" into the end-plates slightly and help to resist expulsion.

The sharp or anti-expulsion edge 8, 108, 108a may be present on the top surface 10, 110, 110a, the bottom surface 20, 120, 120a, 220, or both surfaces of the implant 1, 101, 101a. The anti-expulsion edge 8, 108, 108a may comprise a blade. The sharp or anti-expulsion edge 8, 108, 108a may be oriented toward the anterior portion 40, 140, 140a, the posterior portion 50, 150, 150a, or either of the opposing lateral sides 30, 130, 130a. The orientation of the anti-expulsion edge 8, 108, 108a may depend on the intended orientation of the implant 1, 101, 101a when it has been implanted between vertebrae in the patient.

The sharp or anti-expulsion-edge 8, 108, 108a may comprise an anti-expulsion edge angle E. The anti-expulsion edge angle E may be from about 80 degrees to about 100 degrees. In preferred aspects, the anti-expulsion edge angle E may be measured by taking into account the lordosis angle O of the implant 1, 101, 101a. In highly preferred aspects, the anti-expulsion edge angle E is measured by subtracting half of the lordotic angle O from 90 degrees. For example, where the lordosis angle O of the implant 1, 101, 101a is 12 degrees, the anti-expulsion edge angle E is 84 degrees (90−(12×0.5)). The anti-expulsion edge angle E may be about 80 degrees, about 81 degrees, about 82 degrees, about 83 degrees, about 84 degrees, about 85 degrees, about 86 degrees, about 86.5 degrees, about 87 degrees, about 88 degrees, or about 89 degrees.

Certain embodiments of the invention are particularly suited for use during interbody spinal implant procedures. But the process according to the invention at least substantially reduces, and at least in some cases substantially eliminates the cutting of bone. The process seeks to preserve as much of a vertebral endplate as possible. The process substantially minimizes or eliminates impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load. In contrast, during traditional fusion procedures using other implant types, the vertebral endplate natural arch may be significantly removed due to excessive surface preparation for implant placement and seating.

To insert an implant 1, 101, 101a, the vertebrae may be distracted and the intervertebral space prepared according to any suitable process, while preserving as much vertebral endplate bone as possible. Following preparation of the intervertebral space, a determinatively sized interbody implant 1, 101, 101a may inserted into the prepared disc space, and its location may be adjusted by the practitioner until the implant 1, 101, 101a is at or substantially near to its intended integration location. Once the location is established, the practitioner may insert an expansion wedge 80, 180, 180a into the implant socket 70, 170, 170a, thereby separating each of the top 10, 110, 110a and bottom 20, 120, 120a portions of the implant 1, 101, 101a apart, and increasing the distance between them and the height H of the implant 1, 101, 101a. The expansion wedge 80, 180, 180a preferably comprises a height h suitable to increase the implant height H appropriate for the patient. With the expansion wedge 80, 180, 180a fully inserted into the implant socket 70, 170, 170a, the practitioner may insert an anchor pin 90, 190, 190a into the opening 87, 187, 187a of the expansion wedge 80, 180, 180a, through each channel 86, 186, 186a, and out from each slot 16, 116, 116a, 26, 126, 126a. The anchor pin 90, 190, 190a is preferably of sufficient size, and is inserted sufficiently to engage vertebral endplate bone, and helps resist expulsion of the implant 1. 101, 101a from the intervertebral space. In some aspects, the anchor pin 90, 190, 190a may be further secured in place (in addition to the locking interaction with the teeth/ridges and notch/catch/pawl) within the wedge 80, 180, 180a with an adhesive or a cement such as bone cement.

In some aspects, the implant 1, 101, 101a may be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be pre-loaded into the implant 1, 101, 101a, for example, by filling the vertical aperture 60, 160, 160a before inserting the implant 1, 101, 101a into the intervertebral space. The bone graft material may fill the full volume, or less than the full volume, of the implant interior and surrounding disc space appropriately.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a include smooth, rounded, and highly radiused posterior portions and lateral sides which may minimize extraneous bone removal for endplate preparation and reduce localized stress concentrations. Thus, interbody surgical implant 1, 101, 101a and methods of using it are particularly useful in preserving the natural arch of the vertebral endplate and minimizing the chance of implant subsidence.

Because the endplates are spared during the process of inserting the spinal implant 1, 101, 101a hoop stress of the inferior and superior endplates is maintained. Spared endplates allow the transfer of axial stress to the apophasis. Endplate flexion allows the bone graft placed in the interior of the spinal implant 1, 101, 101 to accept and share stress transmitted from the endplates. In addition, spared endplates minimize the concern that BMP might erode the cancellous bone.

The interbody spinal implant 1, 101, 101a is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1, 101, 101a) to facilitate press-fit implantation. Further, certain embodiments of the current invention having a smooth and rounded posterior portion (and lateral sides) may facilitate easier insertion into the disc space. Still further, those embodiments having a roughened surface topography 18, 118, 118a may lessen the risk of excessive bone removal during distraction as compared to implants having teeth, ridges, or threads currently known in the art even in view of a press-fit surgical distraction method. Nonetheless, once implanted, the interbody surgical implant 1, 101, 101a may provide secure seating and prove difficult to remove, particularly with supporting contributions from the anchor pin 90, 190, 190a.

The invention encompasses a number of different configurations, including a one-piece, titanium-only implant and a composite implant formed of top and bottom plates (components) made out of titanium. The surfaces exposed to the vertebral body are dual acid etched to allow for bony in-growth over time, and to provide resistance against expulsion. The top and bottom titanium plates are assembled together with the implant body that is injection molded with PEEK. The net result is a composite implant that has engineered stiffness for its clinical application. The axial load is borne by the PEEK component of the construct.

The top and bottom surfaces of the implant may be made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

In some aspects, there are no teeth on the top and bottom surfaces. In some aspects, except for certain portions, the implant surfaces, including for example, portions of the top surface 12, 112, 112a and bottom surface 22, 122, 122a may have rounded edges, including blunt and radiused edges. For example, at least a portion of the transverse rim 62, 162, 162a comprises roughened surface topography 18, 118, 118a, but in some aspects, a portion of the transverse rim 62, 162, 162a may comprise a blunt, radiused, and/or round surface that does not comprise roughened surface topography 18, 118, 118a. In some aspects, the posterior face 50, 150, 150a may comprise a generally blunt nosed profile, including a generally rounded profile, and in some aspects, the anterior face 40, 140, 140a may comprise a generally blunt nosed profile. The blunt nose preferably does not comprise roughened surface topography 18, 118, 118a.

It is believed that an intact vertebral end-plate deflects like a diaphragm under axial compressive loads generated due to physiologic activities. If a spinal fusion implant is inserted in the prepared disc space via a procedure which does not destroy the end-plate, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1 according to certain embodiments of the invention allows the vertebral end-plate to deflect and facilitates healing of the bone graft into fusion.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. An interbody spinal implant system, comprising:
    an implant comprising
        a top portion comprising an anterior face, a posterior face, opposing lateral sides, and a top surface comprising a roughened surface topography, and a slot for receiving a prong of an anchor pin extending through the top portion;
        a bottom portion separate from the top portion, the bottom portion comprising an anterior face, a posterior face, opposing lateral sides, and a bottom surface comprising a roughened surface topography, and a slot for receiving a prong of an anchor pin extending through the bottom portion;
        a moveable joint connecting the top portion and bottom portion together and allowing the top and bottom portions to move vertically relative to each other, thereby increasing or decreasing the distance between the top and bottom portions; and
        a socket for receiving an expansion wedge, the socket comprising an opening on either the anterior or posterior face of the top and bottom portions;
    an expansion wedge comprising a top surface, a bottom surface, an anterior face, a posterior face, opposing lateral sides, and an opening on either the anterior face or posterior face for receiving an anchor pin, the opening in communication with a first channel extending through the top surface of the wedge and a second channel extending through the bottom surface of the wedge; and,
    an anchor pin comprising at least two prongs comprising a plurality of ridges or teeth and optionally comprising a roughened surface topography.

2. The interbody spinal implant system of claim 1, wherein the top portion and the bottom portion of the implant further comprise a vertical aperture extending from the top surface through the bottom surface of the implant.

3. The interbody spinal implant system of claim 2, wherein the expansion wedge comprises a vertical aperture extending from the top surface of the wedge to the bottom surface of the wedge, wherein at least a portion of the vertical aperture aligns with the vertical aperture of the implant.

4. The interbody spinal implant system of claim 2, further comprising a bone graft material disposed in the vertical aperture of the implant.

5. The interbody spinal implant system of claim 4, wherein the bone graft material is cancellous autograft bone, allograft bone, demineralized bone matrix (DBM), porous synthetic bone graft substitute, bone morphogenic protein (BMP), or a combination thereof.

6. The interbody spinal implant system of claim 1, wherein the implant is generally oval-shaped in transverse cross-section.

7. The interbody spinal implant system of claim 1, wherein the implant is generally rectangular-shaped in transverse cross-section.

8. The interbody spinal implant system of claim 1, wherein the implant and the expansion wedge are each generally curved-shaped in transverse cross-section.

9. The interbody spinal implant system of claim 2, wherein the vertical aperture defines a first transverse rim surrounding the vertical aperture on the top surface of the implant and a second transverse rim surrounding the vertical aperture on the bottom surface of the implant.

10. The interbody spinal implant system of claim 1, wherein the implant comprises a lordotic angle adapted to facilitate alignment of the spine.

11. The interbody spinal implant system of claim 1, wherein the implant comprises a metal.

12. The interbody spinal implant system of claim 1, wherein the implant comprises a non-metal polymer.

13. The interbody spinal implant system of claim 12, wherein the non-metal polymer comprises polyetherether ketone or ultra-high molecular weight polyethylene.

14. The interbody spinal implant system of claim 1, wherein the top portion of the implant and the bottom portion of the implant further comprises a catch capable of engaging a ridge or tooth on the anchor pin and thereby resisting expulsion of the anchor pin from implant.

15. The interbody spinal implant system of claim 1, wherein the expansion wedge further comprises a spur capable of directing a prong of the anchor pin into each of the first and the second channels.

16. A kit, comprising the interbody spinal implant system of claim 1, a bone graft material, and instructions for using the interbody spinal implant system in a method for repairing a spinal defect in a subject in need thereof.

17. The kit of claim 16, further comprising one or more surgical tools to facilitate implantation of the implant in an intervertebral space of the spine of the subject.

* * * * *